(12) United States Patent
Muramatsu et al.

(10) Patent No.: US 10,632,282 B2
(45) Date of Patent: Apr. 28, 2020

(54) CATHETER ASSEMBLY

(71) Applicant: TERUMO KABUSHIKI KAISHA, Tokyo (JP)

(72) Inventors: Masataka Muramatsu, Yamanashi (JP); Masahiro Ishida, Kanagawa (JP); Shinya Kusunoki, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 242 days.

(21) Appl. No.: 15/713,235

(22) Filed: Sep. 22, 2017

(65) Prior Publication Data

US 2018/0008803 A1 Jan. 11, 2018

Related U.S. Application Data

(63) Continuation of application No. PCT/JP2016/055808, filed on Feb. 26, 2016.

(30) Foreign Application Priority Data

Mar. 25, 2015 (JP) .................................. 2015-062064

(51) Int. Cl.
  *A61M 25/00* (2006.01)
  *A61M 5/158* (2006.01)
  (Continued)

(52) U.S. Cl.
  CPC ........ *A61M 25/0097* (2013.01); *A61M 5/158* (2013.01); *A61M 25/06* (2013.01);
  (Continued)

(58) Field of Classification Search
  CPC ........ A61M 25/0097; A61M 25/09041; A61M 25/065; A61M 5/158; A61M 2005/1585; A61M 39/02; A61M 25/06
  See application file for complete search history.

(56) References Cited

U.S. PATENT DOCUMENTS

| 5,704,914 A | 1/1998 | Stocking et al. |
| 6,171,277 B1* | 1/2001 | Ponzi ................. A61B 18/1492 604/22 |
| 2008/0300574 A1* | 12/2008 | Belson .............. A61M 25/0606 604/510 |

FOREIGN PATENT DOCUMENTS

| JP | 10-099443 | 4/1998 |
| JP | 2008-148737 | 7/2008 |

(Continued)

OTHER PUBLICATIONS

International Search Report issued in International Patent Application No. PCT/JP2016/055808 dated Apr. 26, 2016.

*Primary Examiner* — Bhisma Mehta
*Assistant Examiner* — Hamza A Darb
(74) *Attorney, Agent, or Firm* — Foley & Lardner LLP

(57) ABSTRACT

A catheter assembly includes a catheter; a catheter hub fixed to a proximal end portion of the catheter; a hollow needle having a needle tip and disengageably located in the catheter; a needle hub fixed to a proximal end portion of the needle; a guide wire slidably located in the needle, the guide wire being longer than the catheter and having a distal end that is protrudable from the needle tip; a guide wire hub configured to support the guide wire and move the guide wire with respect to the needle in association with movement of the guide wire hub; and a movement mechanism configured to retract the guide wire hub with respect to the needle hub such that the distal end of the guide wire is housed in the needle in association with forward movement of the catheter hub with respect to the needle hub.

7 Claims, 24 Drawing Sheets

(51) Int. Cl.
    *A61M 25/06* (2006.01)
    *A61M 39/02* (2006.01)
    *A61M 25/09* (2006.01)

(52) U.S. Cl.
    CPC .... *A61M 25/065* (2013.01); *A61M 25/09041* (2013.01); *A61M 39/02* (2013.01); *A61M 2005/1585* (2013.01)

(56) References Cited

FOREIGN PATENT DOCUMENTS

| JP | 2008-200162 | 9/2008 |
| JP | 2009-500129 | 1/2009 |
| JP | 2010-512803 | 4/2010 |
| JP | 2010-526591 | 8/2010 |
| JP | 2013-529111 | 7/2013 |

* cited by examiner

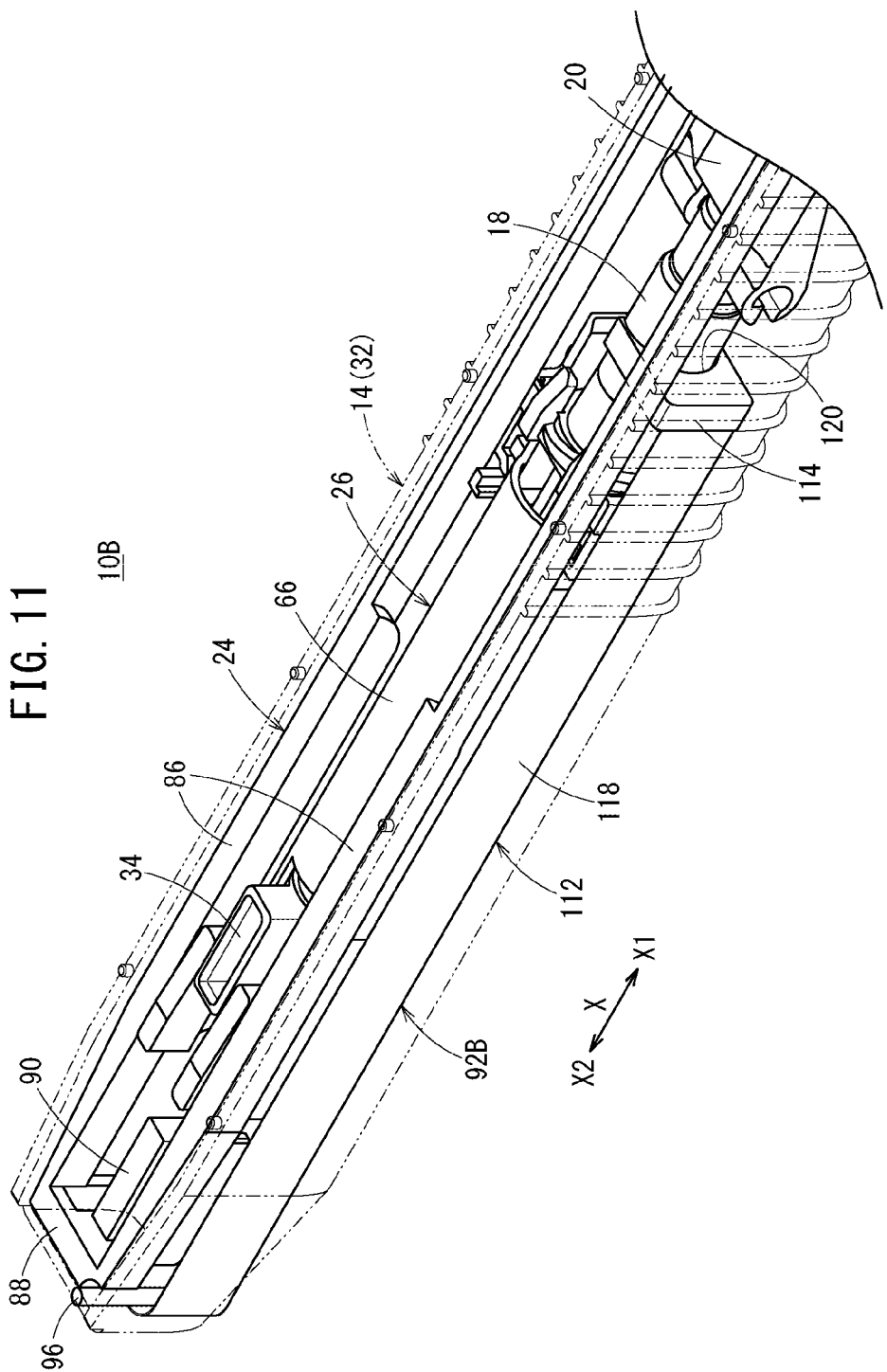

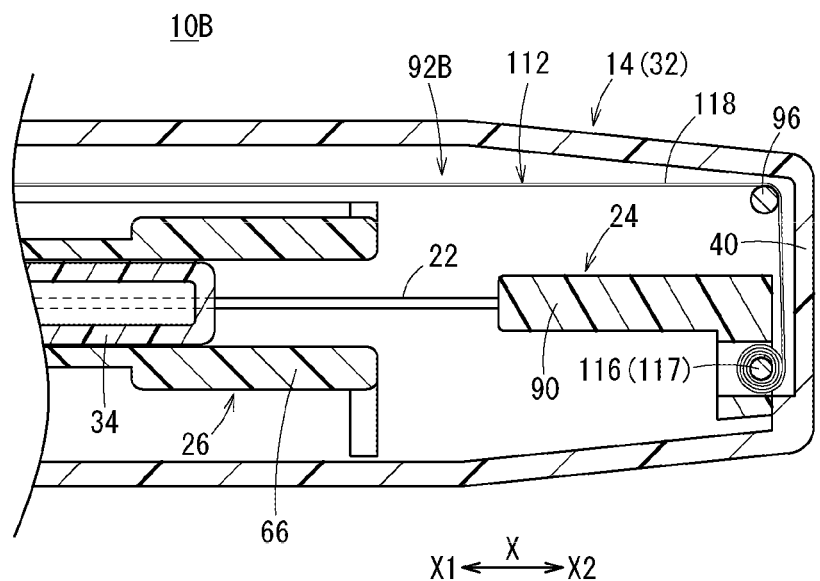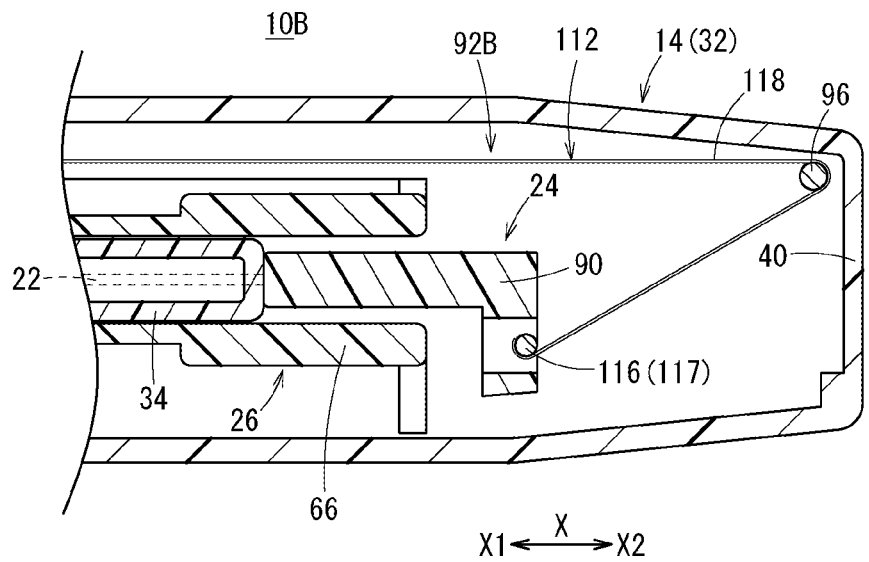

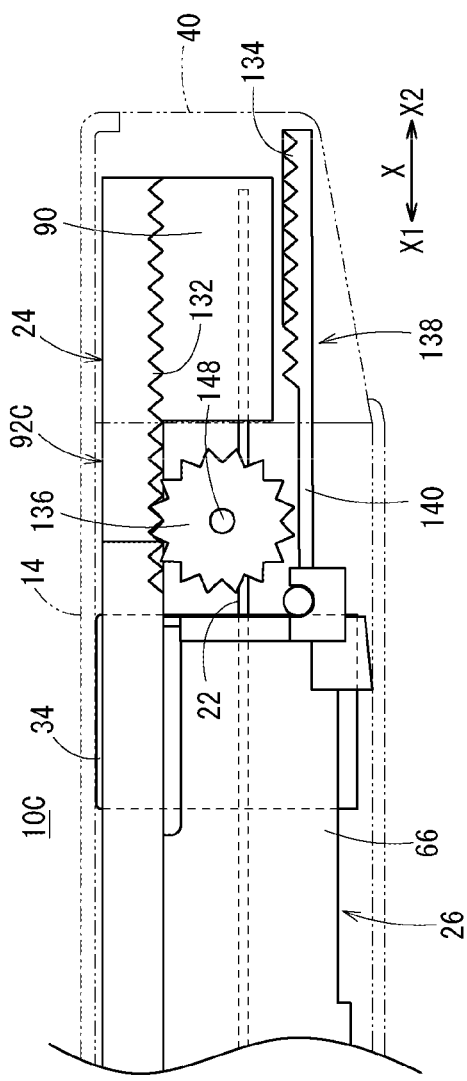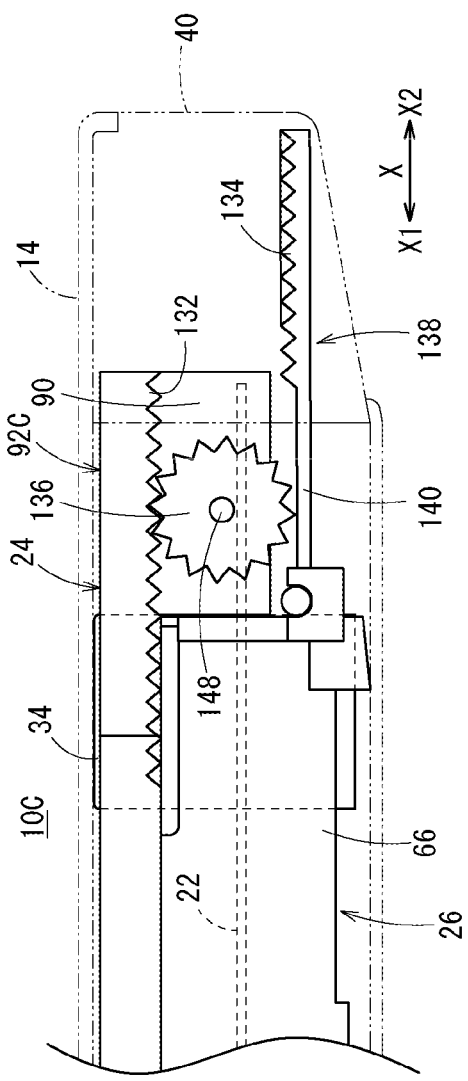

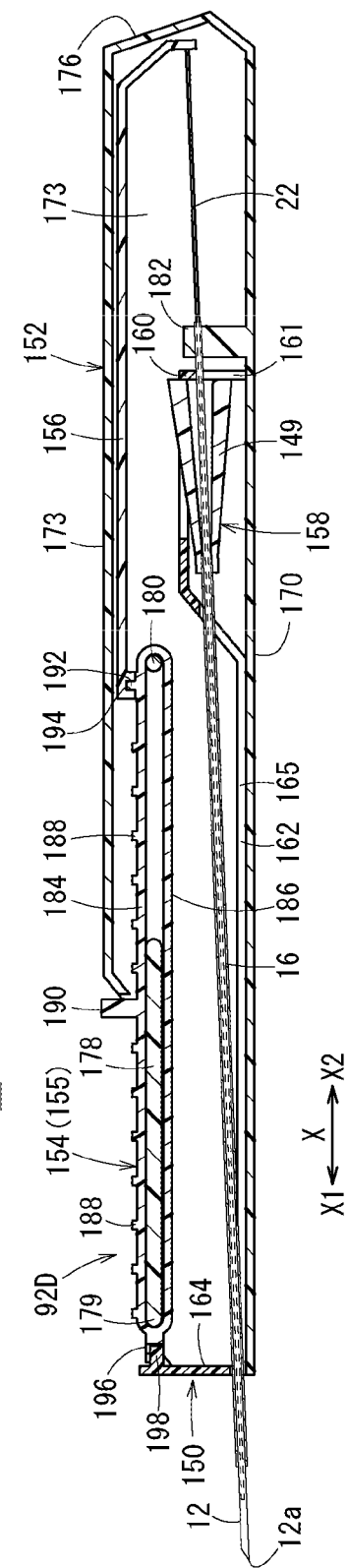

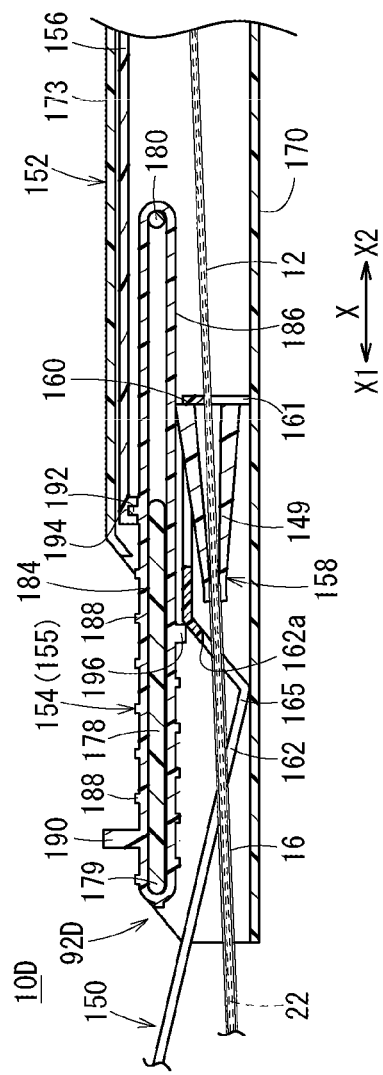
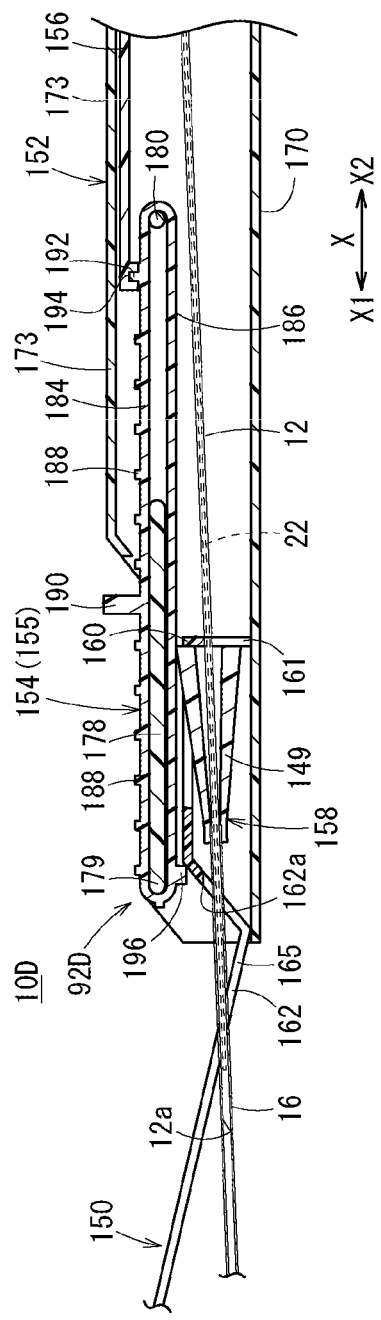

CATHETER ASSEMBLY

CROSS REFERENCE TO RELATED APPLICATIONS

The present application is a bypass continuation of PCT/JP2016/055808, filed on Feb. 26, 2016, which claims priority to Japanese application number 2015-062064, filed on Mar. 25, 2015, the contents of which are hereby incorporated by reference in their entireties.

BACKGROUND

The present disclosure relates to a catheter assembly having that is placed within a blood vessel for fluid transfusion in a patient.

Typically, a catheter assembly is used, for example, for fluid transfusion in a patient. The catheter assembly of this type includes a hollow catheter, a catheter hub fixed to a proximal end of the catheter, a hollow inner needle inserted into the catheter and having a sharp needle tip at a distal end, and a needle hub fixed to a proximal end of the inner needle. The catheter assembly may include, for example, a guide wire slidably inserted into an inner cavity of the inner needle in an axial direction and configured to protrude from a distal end of the inner needle for the purpose of easily inserting the catheter into a blood vessel, as described in JP 2013-529111 A.

SUMMARY

The catheter assembly of JP 2013-529111 A includes a safety member configured to cover the inner needle distal end when the inner needle is removed from the catheter. However, in the catheter assembly of JP 2013-529111 A, a guide wire distal end protrudes from the inner needle distal end in the state in which the inner needle is removed from the catheter. Thus, even in the case of protecting the inner needle distal end by the safety member, the guide wire distal end protrudes from the safety member, and therefore, there is a probability that blood adheres to the guide wire is spattered. If an attempt is made to protect the guide wire distal end by the safety member as well, the entire length of the safety member needs to be increased. Accordingly, an entire product length is increased, leading to a difficulty in use by a user.

Embodiments described in this application have been made in view of such a problem. One object of certain embodiments described in this application is to provide a catheter assembly configured so that spattering of blood adhering to a guide wire can be inhibited.

According to one embodiment, a catheter assembly includes: a catheter; a catheter hub fixed to a proximal end portion of the catheter; a hollow inner needle having a needle tip and disengageably inserted into the catheter; a needle hub fixed to a proximal end portion of the inner needle; a guide wire slidably inserted into the inner needle, being longer than the catheter, and having a distal end protrudable from the needle tip; a guide wire hub configured to support the guide wire and move the guide wire with respect to the inner needle in association with movement; and a movement mechanism configured to retract the guide wire hub with respect to the needle hub such that the distal end of the guide wire is housed in the inner needle in association with forward movement of the catheter hub with respect to the needle hub.

According to the catheter assembly configured as described above, when the catheter hub is moved forward with respect to the needle hub for inserting the catheter into a blood vessel along an outer surface of the guide wire inserted into the blood vessel in advance, the guide wire hub is pulled back under action of the movement mechanism, and the distal end of the guide wire is automatically housed in the inner needle. This can inhibit spattering of the blood adhering to the guide wire.

In the above-described catheter assembly, the movement mechanism may include a force transmitter configured to transmit force to the guide wire hub in association with movement of the catheter hub, and a force direction changer configured to change a direction of the force of the force transmitter.

In the above-described catheter assembly, the movement mechanism may have a movable member configured to move forward with respect to the needle hub in association with the forward movement of the catheter hub with respect to the needle hub, and when the catheter hub moves forward with respect to the needle hub, convert force for forward moving, with respect to the needle hub, the movable member following the catheter hub into force for retracting the guide wire hub with respect to the needle hub.

According to such a configuration, the guide wire can be reliably pulled back by means of movement of the movable member following the catheter hub.

In the above-described catheter assembly, the movement mechanism may include a force transmission member exhibiting flexibility, the force transmission member may have a first end portion coupled with the movable member, a second end portion coupled with the guide wire hub, and a middle portion forming a portion between the first end portion and the second end portion, and the middle portion may be hooked on a support portion provided at the needle hub.

According to such a configuration, when the movable member moves forward with respect to the needle hub, the first end portion coupled with the movable member moves forward, and on the other hand, the second end portion coupled with the guide wire hub retracts. Thus, the force for moving the movable member forward with respect to the needle hub can be efficiently converted into the force for retracting the guide wire hub with respect to the needle hub.

In the above-described catheter assembly, in a state in which the guide wire hub is at an initial position with respect to the needle hub, the middle portion may be loosened to such an extent that forward movement of the guide wire hub with respect to the needle hub is allowed.

According to such a configuration, forward movement of the guide wire hub with respect to the needle hub is not interfered by the force transmission member, and therefore, the guide wire can be inserted into the blood vessel without difficulty.

In the above-described catheter assembly, the first end portion may be disengageably coupled with the movable member through a coupling mechanism, and when the movable member moves forward with respect to the needle hub, the first end portion may be disengaged from the movable member by action of force exceeding coupling retention force between the first end portion and the movable member on the coupling mechanism after the distal end of the guide wire has been housed in the inner needle by retraction of the guide wire hub with respect to the needle hub.

According to such a configuration, forward movement of the movable member with respect to the needle hub is not interfered by the force transmission member, and therefore, the catheter hub can be moved forward with respect to the needle hub without difficulty.

In the above-described catheter assembly, the movement mechanism may be coupled with the catheter hub or a catheter operation member connected to the catheter hub, may be coupled with the guide wire hub, and may convert force for moving the catheter hub or the catheter operation member forward with respect to the needle hub into force for retracting the guide wire hub with respect to the needle hub.

According to such a configuration, the guide wire can be reliably pulled back by means of movement of the catheter hub or the catheter operation member.

In the above-described catheter assembly, the movement mechanism may include a force transmission member exhibiting flexibility, the force transmission member may have a first end portion coupled with the catheter hub or the catheter operation member, a second end portion coupled with the guide wire hub, and a middle portion forming a portion between the first end portion and the second end portion, and the middle portion may be hooked on a support portion provided at the needle hub.

According to such a configuration, the force for moving the catheter hub or the catheter operation member forward with respect to the needle hub can be efficiently converted into the force for retracting the guide wire hub with respect to the needle hub.

In the above-described catheter assembly, in a state in which the guide wire hub is at an initial position with respect to the needle hub, the middle portion may have at least a length allowance for allowing forward movement of the guide wire hub with respect to the needle hub.

According to such a configuration, forward movement of the guide wire hub with respect to the needle hub is not interfered by the force transmission member, and therefore, the guide wire can be inserted into the blood vessel without difficulty.

In the above-described catheter assembly, the movement mechanism may have a gear mechanism configured to convert, through a gear, forward movement of the movable member with respect to the needle hub into retraction movement of the guide wire hub with respect to the needle hub.

According to such a configuration, the force for moving the movable member forward with respect to the needle hub can be efficiently converted into the force for retracting the guide wire hub with respect to the needle hub.

In the above-described catheter assembly, the gear mechanism may have a first rack portion configured to move together with the guide wire hub, a second rack portion configured to move together with the movable member, and a gear wheel provided at the needle hub, and when the movable member moves forward with respect to the needle hub, force of forward movement of the second rack portion may be transmitted to the first rack portion through the gear wheel, and accordingly, the first rack portion retracts.

According to such a configuration, the gear mechanism configured to retract the guide wire hub in association with forward movement of the movable member can be built with a simple configuration.

In the above-described catheter assembly, in a state in which the second rack portion is at an initial position with respect to the needle hub, the second rack portion may not engage with the gear wheel, and the second rack portion may engage with the gear wheel after the second rack portion has moved forward with respect to the needle hub by a predetermined distance.

According to such a configuration, forward movement of the guide wire hub with respect to the needle hub is not interfered by the gear mechanism, and therefore, the guide wire can be inserted into the blood vessel without difficulty.

In the above-described catheter assembly, the movable member may be a member forming at least a portion of a protector, and the protector may be disengageably coupled with the catheter hub, may be movable relative to the needle hub in an axial direction, and may cover at least the needle tip of the inner needle in association with removal of the inner needle from the catheter.

With this configuration, in the catheter assembly including the protector, movement of the protector operating in association with forward movement of the catheter hub with respect to the needle hub is utilized so that the distal end of the guide wire can be automatically pulled back into the inner needle when the guide wire is removed from the inner needle.

In the above-described catheter assembly, further including a catheter operation member connected to the catheter hub, the movement mechanism may be in a form of an endless wire operation member exhibiting flexibility, the wire operation member may be coupled with the guide wire hub, may be disposed at the needle hub with the wire operation member being exposed through the needle hub, and may be configured such that a portion of the wire operation member exposed through the needle hub is operable in a distal end direction, the wire operation member may be provided with a protrusion protruding into the needle hub with the guide wire protruding from the needle tip, and when the catheter is moved forward with respect to the needle hub, the wire operation member may be driven such that the catheter hub or the catheter operation member pushes the protrusion in the distal end direction to move a distal end portion of the guide wire with respect to the inner needle toward a proximal end side of a distal end opening of the inner needle.

According to such a configuration, the force for moving the catheter hub or the catheter operation member forward with respect to the needle hub can be efficiently converted into the force for retracting the guide wire hub with respect to the needle hub.

In the above-described catheter assembly, when the catheter is moved forward with respect to the inner needle with a predetermined length of the distal end portion of the guide wire protruding from the needle tip, the movement mechanism may retract the guide wire hub with respect to the needle hub after the catheter has moved forward with respect to the guide wire by a predetermined distance.

According to such a configuration, when the catheter is inserted into the blood vessel, the guide wire begins retracting after the catheter has been inserted into the blood vessel along the outer surface of the guide wire. Thus, the guide wire can be pulled back in association with the operation of moving out the catheter without interference of a guide function of the guide wire.

According to certain embodiments of the catheter assembly described in this application, spattering of the blood adhering to the guide wire can be inhibited.

BRIEF DESCRIPTION OF THE DRAWINGS

FIG. 11 is a perspective view of a main portion of a catheter assembly of a second embodiment of the present invention.

FIG. 14A is a first view for describing action of the movement mechanism of the catheter assembly illustrated in FIG. 11, and FIG. 14B is a second view for describing action of the movement mechanism of the catheter assembly illustrated in FIG. 11.

FIG. 17A is a first view for describing action of a movement mechanism of the catheter assembly illustrated in FIG. 16, and FIG. 17B is a second view for describing action of the movement mechanism of the catheter assembly illustrated in FIG. 16.

FIG. 22A is a sectional view (a first view for describing a use method) of an initial state of the catheter assembly illustrated in FIG. 19, and FIG. 22B is a second view for describing the method for using the catheter assembly illustrated in FIG. 19.

FIG. 23A is a third view for describing the method for using the catheter assembly illustrated in FIG. 19, and FIG. 23B is a fourth view for describing the method for using the catheter assembly illustrated in FIG. 19.

DETAILED DESCRIPTION

Figure 1:
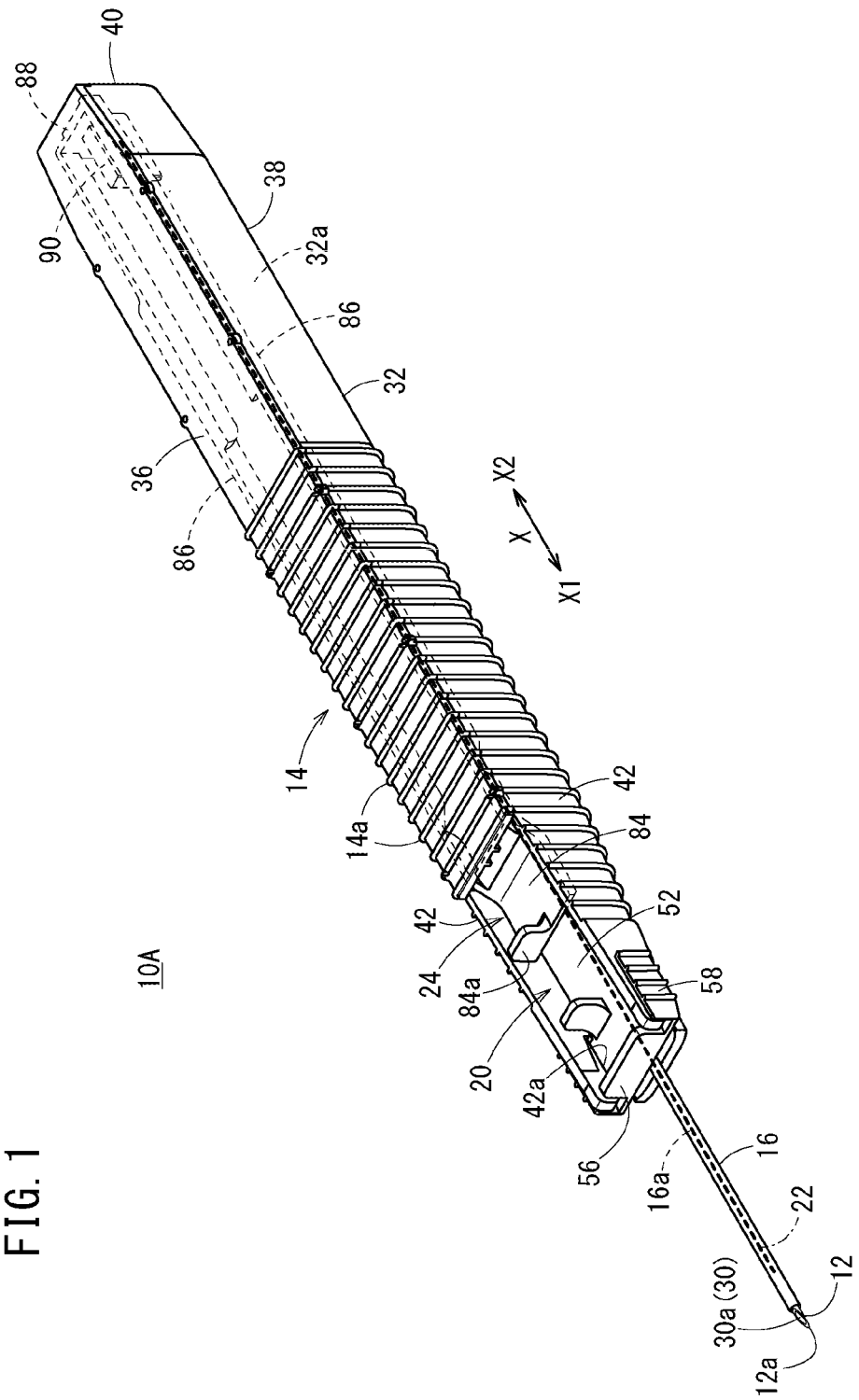
FIG. 1 is a perspective view of an initial state of a catheter assembly of a first embodiment of the present invention.

First to fourth embodiments of a catheter assembly will be described below, with reference to the drawings. In the first to fourth embodiments, the same reference numerals are used to represent elements having identical or similar functions and exhibiting identical or similar advantageous effects in the first to fourth embodiments, and overlapping description will not be repeated. In each figure illustrating the catheter assembly and components thereof, an X-direction indicates an axial direction of the catheter assembly, and specifically, an X1 direction and an X2 direction respectively indicate a distal end direction and a proximal end direction.

First Embodiment

A catheter assembly 10A of the first embodiment illustrated in FIG. 1 is a tool used to perform fluid transfusion, blood transfusion, etc. for a patient (a biological body) and serving as, for example, a medical solution administration unit with which a patient's body is punctured and a portion of which is placed inside the patient's body. Specifically, the catheter assembly 10A has, for improvement of usability of a user such as a doctor or a nurse, the function of delivering out a guide wire 22 through the inside of an inner needle 12.

The catheter assembly 10A can be configured as a catheter (e.g., a central venous catheter, a PICC, and a midline catheter) longer than a peripheral venous catheter. Note that the catheter assembly 10A may be configured as a peripheral venous catheter. Moreover, the catheter assembly 10A is not limited to venous catheters, and may be configured as an arterial catheter such as a peripheral arterial catheter.

The catheter assembly 10A includes the inner needle 12, a housing 14 (an inner needle hub), a catheter 16, a catheter hub 18, a catheter operation member 20, the guide wire 22, a guide wire hub 24, and a protector 26.

The catheter assembly 10A is used as follows.

In an initial state of the catheter assembly 10A illustrated in FIG. 1, the inner needle 12 and the catheter 16 protrude from a distal end of the housing 14 with the inner needle 12 and the catheter 16 overlapping with each other and the guide wire 22 being inserted to the proximal end side of a needle tip 12a in the inner needle 12. Moreover, the catheter hub 18, a proximal end portion of the catheter 16, the catheter operation member 20, the guide wire hub 24, and the protector 26 are housed in the housing 14.

Figure 2:
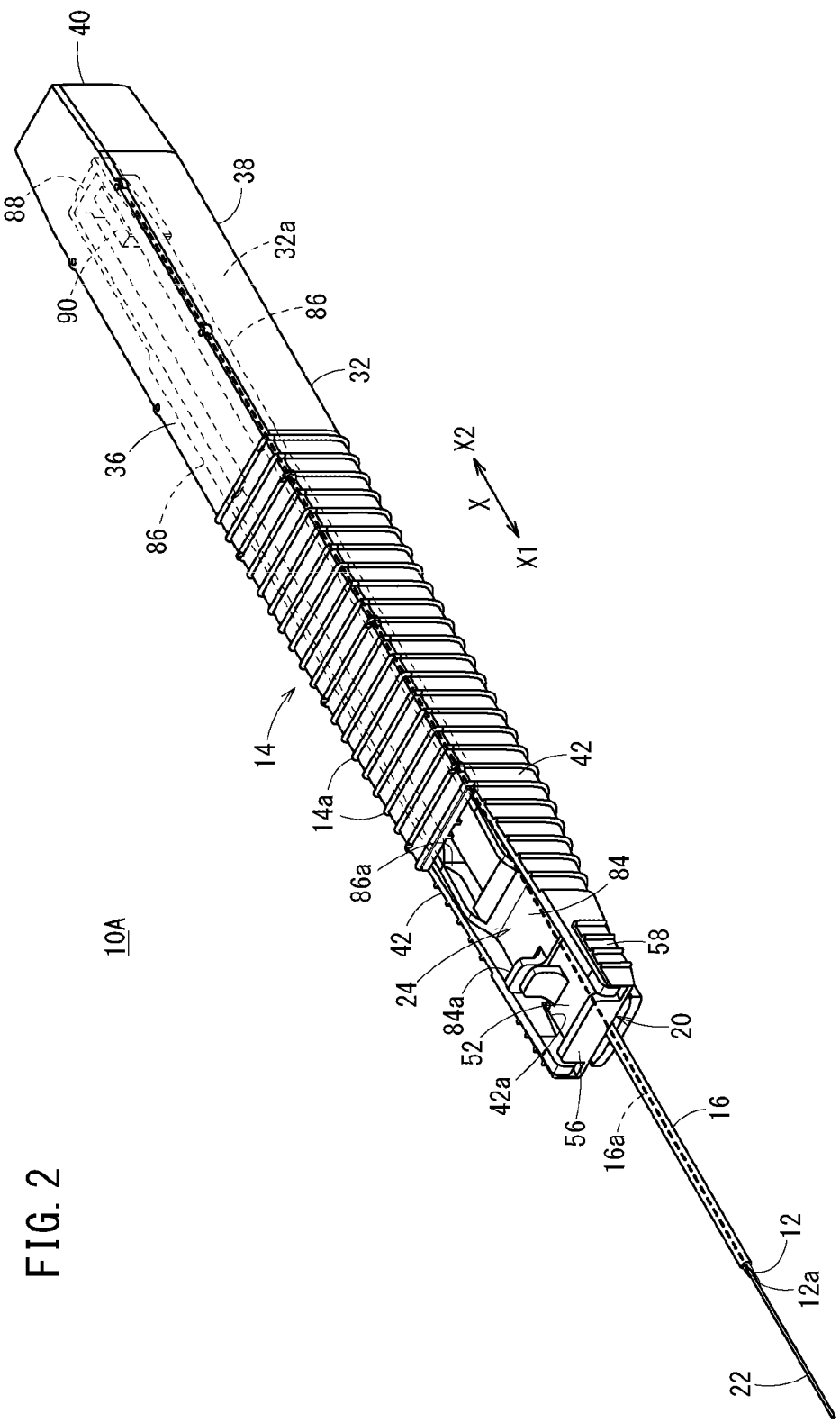
FIG. 2 is a perspective view of a guide wire move-out state of the catheter assembly illustrated in FIG. 1.

In use of the catheter assembly 10A, the user grips the housing 14 to puncture a patient's blood vessel (the vein or the artery) with distal ends of the inner needle 12 and the catheter 16. Further, the user operates, as illustrated in FIG. 2, the guide wire hub 24 to move out relative to the housing 14 in the distal end direction with the puncturing state being maintained, and in this manner, delivers the guide wire 22 out of the needle tip 12a. The guide wire 22 delivered out of the needle tip 12a moves deep in the blood vessel.

Subsequently, the user moves out the catheter hub 18 relative to the housing 14, and in this manner, the catheter 16 further moves in toward the distal end side (that is, deeper in the blood vessel) with respect to the inner needle 12. In this state, the catheter 16 is inserted into the blood vessel along the guide wire 22 moved in the blood vessel in advance. Next, the user holds the position of the catheter 16 inserted into the blood vessel while pulling the housing 14 in the proximal end direction. In this manner, the inner needle 12 is removed from the catheter 16.

Figure 3:
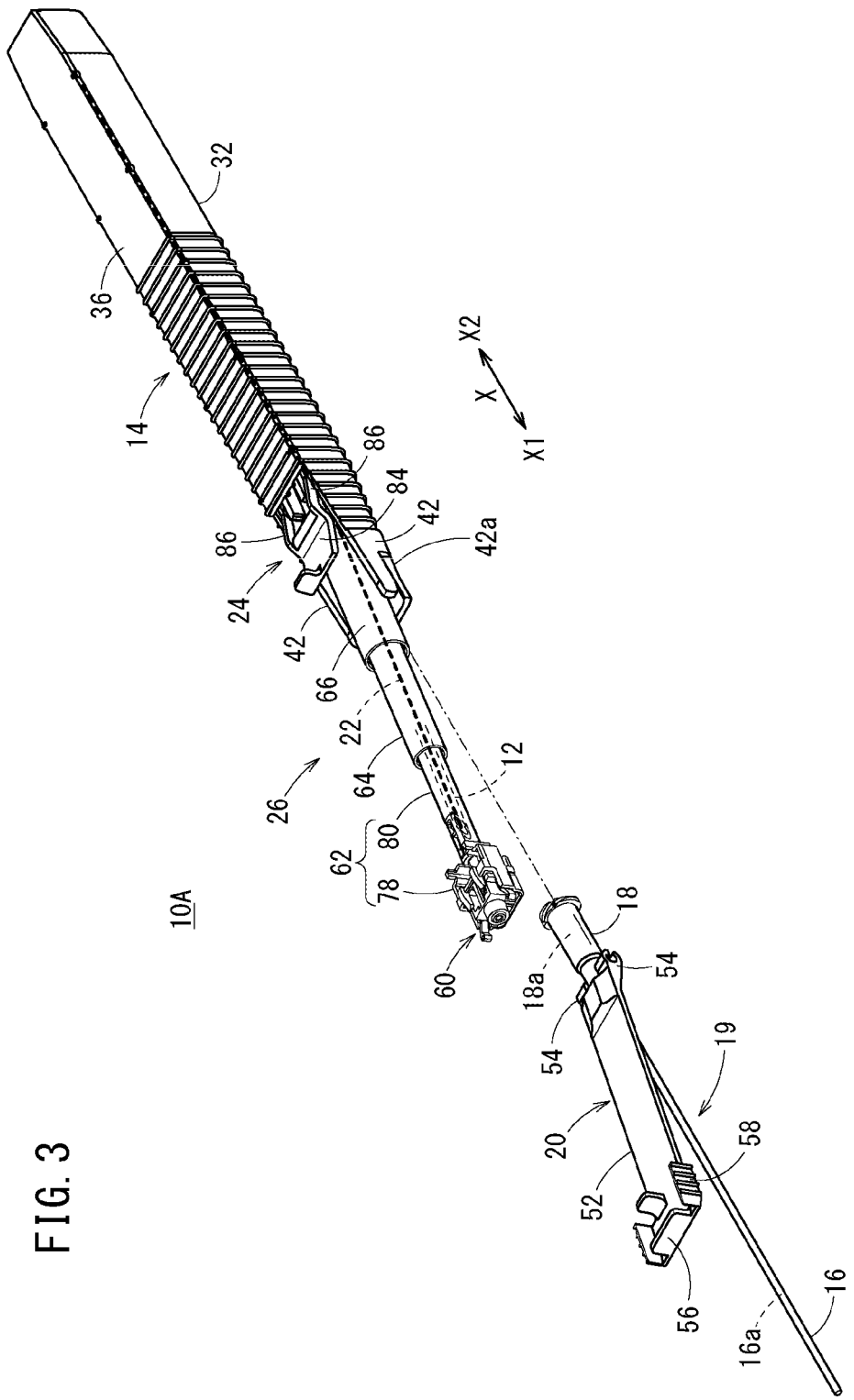
FIG. 3 is a perspective view of a state in which a protector and a catheter hub of the catheter assembly illustrated in FIG. 1 are separated from each other.

In association with the operation of moving the catheter hub 18 out of the housing 14 and the operation of retracting the housing 14 with respect to the catheter hub 18, the protector 26 is extended such that the inner needle 12 is housed in the protector 26, as illustrated in FIG. 3. Thus, the protector 26 inhibits exposure of the inner needle 12 to the outside, thereby inhibiting erroneous puncturing, blood contamination, etc. Moreover, the protector 26 releases the held catheter hub 18 such that the catheter 16 and the catheter hub 18 are placed. The catheter assembly 10A will be specifically described below.

Figure 4:
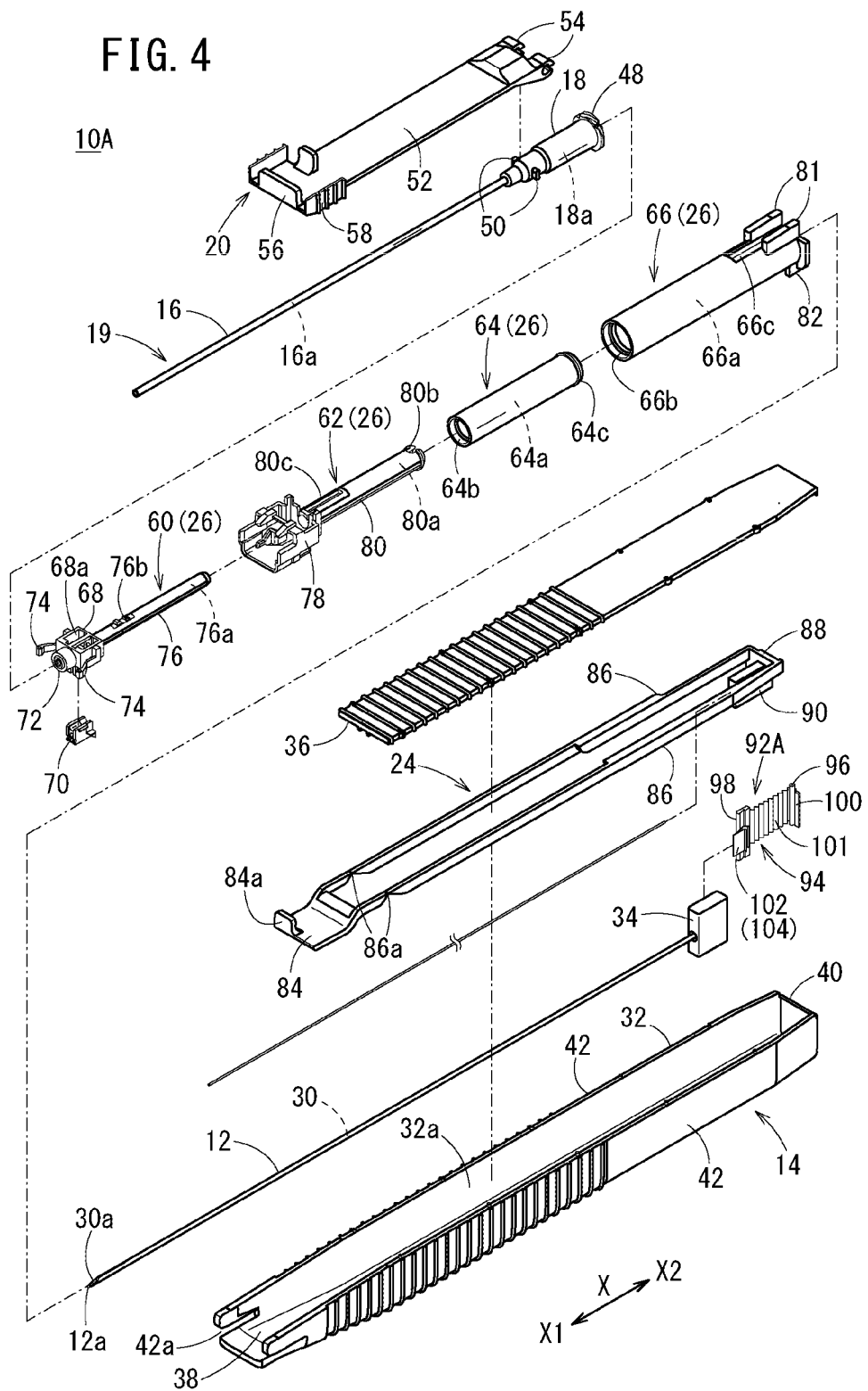
FIG. 4 is an exploded perspective view of the catheter assembly illustrated in FIG. 1.

As illustrated in FIGS. 1 and 4, the inner needle 12 of the catheter assembly 10A is configured as a hollow tubular body exhibiting such stiffness that the skin of the biological body can be punctured with the inner needle 12. The sharp needle tip 12a is formed at the distal end of the inner needle 12. A through-hole 30 is provided along the axial direction in the inner needle 12. The through-hole 30 communicates with a distal end opening 30a provided at the needle tip 12a and a proximal end opening provided at a proximal end of the inner needle 12. Note that a groove portion may be provided along the axial direction at the inner needle 12.

The inner needle 12 is firmly fixed to the housing 14 by an optional fixing method (fusion, bonding, insert molding, etc.). A material forming the inner needle 12 includes, for example, metal materials such as stainless steel, aluminum or aluminum alloy, and titanium or titanium alloy; hard resin; and ceramics.

The housing 14 is formed in a cylindrical shape with such thickness and length that the user can easily grip and operate the housing 14. An outer peripheral surface extending from the vicinity of the distal end to a middle portion of the housing 14 in the axial direction is provided with a plurality of ribs 14a extending around the outer peripheral surface in a circumferential direction so that the user can easily grip the housing 14. The housing 14 includes a housing body 32 having an internal space 32a, a needle holding portion 34 configured to hold a proximal end portion of the inner needle 12 and disposed in the internal space 32a, and a lid body 36 covering an upper side of the internal space 32a such that the lid body 36 and the housing body 32 together form an outer appearance of the housing 14.

The housing body 32 has an elongated bowl shape formed by a lower wall 38, a back wall 40, and a pair of side walls 42, and forms the internal space 32a inside. The lower wall 38 gently inclines, on the distal end side thereof, upward in the distal end direction, and therefore, the internal space 32a becomes shallower in the distal end direction.

Moreover, the back wall 40 and the pair of side walls 42 protrude upward from sides of the lower wall 38, and upper sides of the back wall 40 and the pair of side walls 42 are formed at the same height. The lid body 36 is attached to the upper sides of the back wall 40 and the pair of side walls 42. The pair of side walls 42 is, on the distal end side thereof, provided with cutout portions 42a into which lateral operation portions 58 of the catheter operation member 20 are respectively inserted.

The needle holding portion 34 is fixed to the lower wall 38 of the housing body 32. Note that the needle holding portion 34 may be a portion molded integrally with the housing body 32. Moreover, the needle holding portion 34 is not limited to the configuration of holding a most proximal end portion of the inner needle 12, and may be configured to hold a proximal-end-side outer peripheral surface of the inner needle 12. That is, the most proximal end portion of the inner needle 12 may protrude toward the proximal end side with respect to the needle holding portion 34.

The housing 14 (the housing body 32, the needle holding portion 34, the lid body 36) is preferably made of a relatively-hard material so that the user can easily operate the housing 14. For example, a material forming the housing 14 preferably includes, but not limited to, thermoplastic resin such as polypropylene, polycarbonate, polyamide, polysulfone, polyarylate, and methacrylate-butylene-styrene copolymer.

The catheter 16 of the catheter assembly 10A is in the form of a tubular body exhibiting more flexibility than that of the inner needle 12. An inner cavity 16a in which the inner needle 12 is housed and through which a medical solution, blood, etc. can circulate is formed to penetrate the inside of the catheter 16 along the axial direction. The length of the catheter 16 is not specifically limited, and is optionally set according to a use application, conditions, etc. The length of the catheter 16 is, for example, set to about 20 to 500 mm, about 30 to 400 mm, or about 100 to 300 mm.

For example, a material forming the catheter 16 preferably includes, but not limited to, a soft resin material including fluorine-based resin such as polytetrafluoroethylene (PTFE), ethylene-tetrafluoroethylene copolymer (ETFE), and perfluoroalkoxy alkane (PFA); olefin-based resin such as polyethylene and polypropylene or a mixture thereof; and polyurethane, polyester, polyamide, polyether nylon resin, and a mixture of the olefin-based resin and ethylene-vinyl acetate copolymer.

The proximal end portion of the catheter 16 is fixed to an inner distal end portion of the catheter hub 18 by an optional fixing method (swaging, fusion, bonding, etc.). The catheter hub 18 is exposed on the skin of the patient with the catheter 16 being inserted into the blood vessel. The catheter hub 18 is bonded onto the skin with a tape etc. such that the catheter hub 18 is placed together with the catheter 16. The catheter 16 and the catheter hub 18 form a catheter member 19.

The catheter hub 18 is made of a material harder than the catheter 16, and is formed in a cylindrical shape tapered in the distal end direction. For example, the material described as the example of the material forming the housing 14 may be optionally employed to form the catheter hub 18. A not-shown fluid transfusion tube connector can be connected to the proximal end side of the catheter hub 18.

Figure 5:
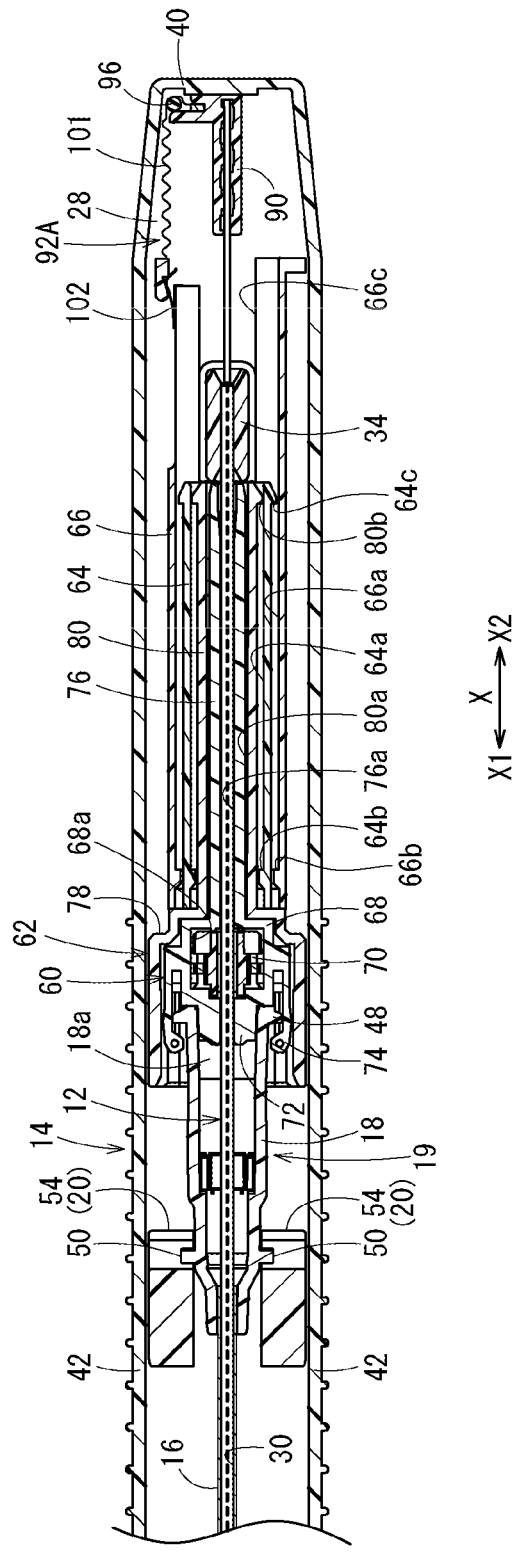
FIG. 5 is a perspective sectional view of a main portion of the catheter assembly illustrated in FIG. 1.

As illustrated in FIG. 5, a hollow portion 18a communicating with the inner cavity of the catheter 16 so that circulation of a transfusion material is allowed is provided in the catheter hub 18. A hemostasis valve, plug, or the like (not shown) is housed in the hollow portion 18a for inhibiting blood backflow upon puncturing with the inner needle 12 and allowing fluid transfusion in association with insertion of the fluid transfusion tube connector. Moreover, a proximal-end-side outer peripheral surface of the catheter hub 18 is provided with a protruding ring-shaped flange portion 48. Further, the outer peripheral surface of the catheter hub 18 is provided with a pair of connection protrusions 50 rotatably connected to the catheter operation member 20.

The catheter operation member 20 is attached to the upper side of the catheter hub 18 so that the user can perform the operation of moving in and out the catheter 16 and the catheter hub 18. In the catheter operation member 20, a body portion 52 extending in the axial direction is formed in a flat plate shape. A proximal end portion of the body portion 52 is provided with a pair of connection pieces 54 detachable from the pair of connection protrusions 50, and a distal end portion of the body portion 52 is provided with an upper operation portion 56 and the lateral operation portions 58 for user's operation of the catheter operation member 20.

Engagement of the connection pieces 54 with the connection protrusions 50 in a state parallel to the axial direction of the catheter hub 18 is held so that separation of the catheter operation member 20 from the catheter hub 18 is inhibited. On the other hand, the connection protrusions 50 and the connection pieces 54 engaging with each other are released by a change in the angle of the catheter operation member 20 with respect to the catheter hub 18 (e.g., the catheter operation member 20 becomes perpendicular to the axial direction of the catheter hub 18). Thus, the catheter operation member 20 can be separated from the catheter hub 18.

As illustrated in FIGS. 4 and 5, the protector 26 includes a plurality of cylindrical bodies (four cylindrical bodies in the present embodiment). In the initial state, the cylindrical bodies overlap with each other on the same axis, thereby showing a shortened state (a multi-layered structure). These cylindrical bodies are housed in the internal space 32a of the housing 14. Moreover, in this state, a distal end portion of the protector 26 stops the catheter hub 18. When the inner needle 12 is disengaged (removed) from the catheter 16, the cylindrical bodies are extended in the distal end direction in a stepwise manner. Thus, the distal end portion of the protector 26 releases the stopped catheter hub 18 with the inner needle 12 being housed in the cylindrical bodies (also see FIG. 3). The cylindrical bodies will be referred to as an inner cylinder 60, an outer cylinder 62, a first relay cylinder 64, and a second relay cylinder 66 (a movable member) in this order from the cylindrical body positioned at the distal end upon extension.

The inner cylinder 60 of the protector 26 includes a block housing portion 68 provided with a cavity portion 68a, a block member 70 movably housed in the cavity portion 68a, a head portion 72 protruding short from the block housing portion 68 in the distal end direction, a pair of elastically-deformable engagement arms 74 protruding from both side surfaces of the block housing portion 68 in the distal end direction, and a first cylinder extension 76 protruding from the block housing portion 68 in the proximal end direction.

The block member 70 is, in the initial state, disposed below the cavity portion 68a with upward displacement of the block member 70 being restricted by the inner needle 12 passing through the cavity portion 68a. Under action of contact between the block member 70 and a not-shown inclined guide surface provided at the outer cylinder 62, the block member 70 inhibits the inner cylinder 60 from moving relative to the outer cylinder 62 in the distal end direction. When the distal end of the inner needle 12 moves to the proximal end side with respect to the block member 70 in association with removal of the inner needle 12 from the catheter 16, the block member 70 becomes upwardly movable, and therefore, the inner cylinder 60 becomes movables relative to the outer cylinder 62 in the distal end direction. Then, when the outer cylinder 62 moves out relative to the inner cylinder 60, the block member 70 is guided by the guide surface of the outer cylinder 62 to move upward, and then, is stopped at an optional height. At this stopped position, the block member 70 faces the needle tip 12a housed in the first cylinder extension 76. This inhibits the inner needle 12 from being exposed through the distal end of the protector 26.

The head portion 72 is detachably inserted and fitted into the hollow portion 18a of the catheter hub 18. In the initial state of the catheter assembly 10A, the engagement arms 74 are housed in a distal end portion (a later-described distal end case portion 78) of the outer cylinder 62 with distal ends of the engagement arms 74 engaging with the flange portion 48 of the catheter hub 18, and therefore, opening of the engagement arms 74 is inhibited. When the inner cylinder 60 moves relative to the outer cylinder 62 in the distal end direction, the engagement arms 74 open while protruding from the distal end portion of the outer cylinder 62. Accordingly, the engagement arms 74 engaging with the catheter hub 18 are released, and the protector 26 including the inner cylinder 60 can be disengaged from the catheter hub 18.

The first cylinder extension 76 has an inner-cylinder-side housing space 76a formed to penetrate the first cylinder extension 76 such that the inner needle 12 is slidably housed and communicating with the cavity portion 68a. Moreover, an outer peripheral surface of the first cylinder extension 76 is provided with an upwardly-protruding protrusion 76b.

The outer cylinder 62 has the distal end case portion 78 formed on the distal end side in a box shape opening at a distal end and an upper portion thereof, and a second cylinder extension 80 extending from the distal end case portion 78 in the proximal end direction. In the initial state, the distal end case portion 78 houses the block housing portion 68, the engagement arms 74, and the block member 70 of the inner cylinder 60.

The second cylinder extension 80 has an outer-cylinder-side housing space 80a formed to penetrate the second cylinder extension 80 such that the first cylinder extension 76 is slidably housed and communicating with a space of the distal end case portion 78. A proximal-end-side outer peripheral surface of the second cylinder extension 80 is provided with an outwardly-protruding outer-cylinder-side outwardly-raised portion 80b. Moreover, a long hole 80c communicating with the outer-cylinder-side housing space 80a is formed at an upper portion of the second cylinder extension 80. The protrusion 76b of the first cylinder extension 76 is disposed in the long hole 80c, and therefore, the long hole 80c inhibits detachment from the outer cylinder 62 when the inner cylinder 60 moves out.

The first relay cylinder 64 includes a first-relay-cylinder-side housing space 64a formed to penetrate the first relay cylinder 64 such that the second cylinder extension 80 is slidably housed. A distal-end-side inner peripheral surface of the first-relay-cylinder-side housing space 64a is provided with an inwardly-protruding ring-shaped first-relay-cylinder-side inwardly-raised portion 64b. When the outer cylinder 62 moves out relative to the first relay cylinder 64 upon disengagement, the outer-cylinder-side outwardly-raised portion 80b is caught by the first-relay-cylinder-side inwardly-raised portion 64b such that detachment of the outer-cylinder-side outwardly-raised portion 80b is inhibited. Moreover, a proximal-end-side outer peripheral surface of the first relay cylinder 64 is provided with an outwardly-protruding first-relay-cylinder-side outwardly-raised portion 64c.

The second relay cylinder 66 has a second-relay-cylinder-side housing space 66a formed to have an entire length longer than that of the first relay cylinder 64 and formed to penetrate the second relay cylinder 66 such that the first relay cylinder 64 is slidably housed. A distal-end-side inner peripheral surface of the second-relay-cylinder-side housing space 66a is provided with an inwardly-protruding ring-shaped second-relay-cylinder-side inwardly-raised portion 66b. When the first relay cylinder 64 moves out relative to the second relay cylinder 66 upon disengagement, the first-relay-cylinder-side outwardly-raised portion 64c is caught by the second-relay-cylinder-side inwardly-raised portion 66b such that detachment of the first-relay-cylinder-side outwardly-raised portion 64c is inhibited.

Moreover, a proximal-end-side outer peripheral surface of the second relay cylinder 66 is provided with a pair of upwardly-protruding upper guide protrusions 81 and a pair of downwardly-protruding lower guide protrusions 82. The pair of upper guide protrusions 81 is guided by a not-shown projection formed on a lower surface of the lid body 36. The pair of lower guide protrusions 82 is inserted into and guided by a not-shown guide groove of the housing body 32. When the second relay cylinder 66 moves out, the pair of lower guide protrusions 82 comes into contact with a distal end edge of the guide groove, thereby inhibiting detachment of the second relay cylinder 66 from the housing 14.

Further, on the proximal end side of the second relay cylinder 66, slits 66c are provided from a proximal end of the second relay cylinder 66 in the distal end direction. The slits 66c are formed in pair at upper and lower portions of a peripheral wall of the second relay cylinder 66, and in the initial state, the needle holding portion 34 is disposed in the slits 66c (see FIG. 5).

Referring back to FIG. 1, the guide wire hub 24 is configured to support the guide wire 22 and move the guide wire 22 relative to the inner needle 12 in association with movement of the guide wire hub 24. In the present embodiment, the guide wire hub 24 is fixed to a proximal end portion of the guide wire 22. The guide wire hub 24 includes a distal-end-side operation plate portion 84, a pair of extensions 86 extending from the operation plate portion 84 in the proximal end direction, a bridge portion 88 configured to bridge between proximal ends of the pair of extensions 86, and a wire holding portion 90 protruding from the bridge portion 88 to fix and hold the proximal end portion of the guide wire 22.

The operation plate portion 84 is disposed on an upper surface of the catheter operation member 20 at an exposed portion of the operation plate portion 84 through the housing 14 on the distal end side with respect to the lid body 36. The operation plate portion 84 inclines, on the proximal end side thereof, upward in the proximal end direction, and the pair of right and left extensions 86 are coupled respectively to both sides of the operation plate portion 84. Moreover, an upper distal end portion of the operation plate portion 84 is provided with a protruding operation piece 84a for user's operation of the guide wire hub 24.

The pair of extensions 86 extends from the operation plate portion 84 in the proximal end direction by the substantially same length as the entire length (the longitudinal length) of the lid body 36 of the housing 14. Hinge portions 86a (see FIG. 4) are provided closer to the distal end side at the pair of extensions 86, and freely change the angle of the operation plate portion 84 with respect to the extensions 86. Thus, the operation plate portion 84 diagonally inclines when the catheter operation member 20 and the protector 26 move out, and does not interfere with the operation of moving out the catheter operation member 20 and the operation of extending the protector 26 (see FIG. 3).

Figure 6:
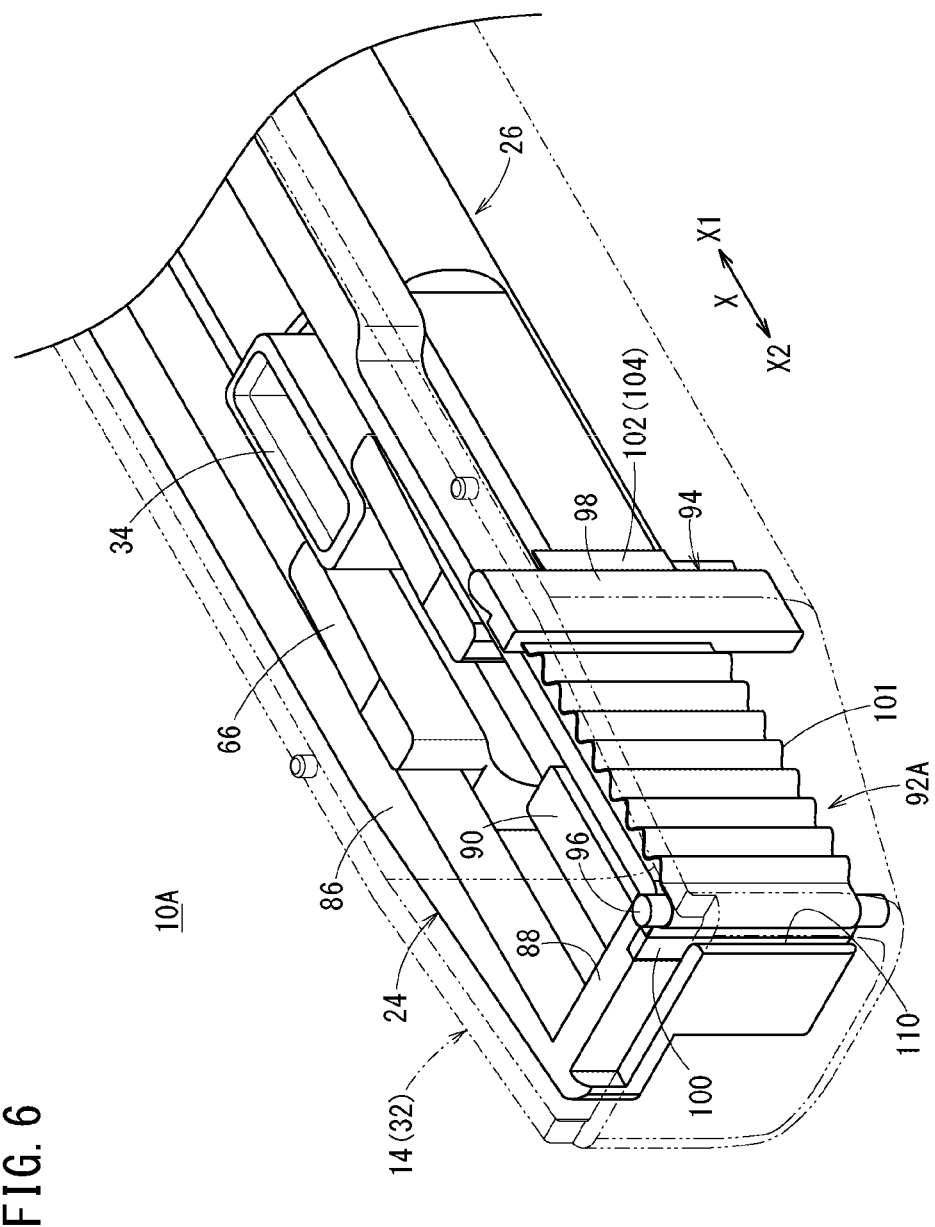
FIG. 6 is a view for describing a structure of a movement mechanism of the catheter assembly illustrated in FIG. 1.

As illustrated in FIG. 6, the catheter assembly 10A further includes a movement mechanism 92A configured to retract the guide wire hub 24 relative to the housing 14 such that a distal end of the guide wire 22 is housed in the inner needle 12 in association with forward movement of the catheter hub 18 with respect to the housing 14.

In the present embodiment, the movement mechanism 92A includes a force transmitter configured to transmit force to the guide wire hub 24 in association with movement of the catheter hub 18, and a force direction changer configured to change the direction of force of the force transmitter. In the present embodiment, the force transmitter includes a force transmission member 94 and a member interposed between the catheter hub 18 and the force transmission member 94. The interposed member is the protector 26. More specifically, the force transmission member 94 is a film 101. The force direction changer is a support rod 96 as a support portion. The force transmitter transmits, to the guide wire hub 24, force accompanied by movement in the direction of moving the catheter hub 18 forward with respect to the housing 14. Meanwhile, the force in the forward movement direction at a portion of the force transmitter is changed by the force direction changer. The force in the changed direction is transmitted to other portions of the force transmitter. The force transmitted to the other portions of the force transmitter retracts the guide wire hub 24.

In the present embodiment, the movement mechanism 92A is configured such that when the catheter hub 18 moves forward with respect to the housing 14, the force for forward moving, with respect to the housing 14, the second relay cylinder 66 (the movable member) following the catheter hub 18 is converted into the force for retracting the guide wire hub 24 with respect to the housing 14.

Specifically, the movement mechanism 92A has the second relay cylinder 66 forming the movable member, the force transmission member 94 coupled with the second relay cylinder 66 and the guide wire hub 24 and exhibiting flexibility, and the support rod 96 (the support portion) which is fixed to the housing 14 and on which the force transmission member 94 is hooked. The force transmission member 94 and the support rod 96 are arranged in the housing 14. The support rod 96 is disposed on the proximal end side in the housing 14.

The force transmission member 94 has a first end portion 98 coupled with the second relay cylinder 66, a second end portion 100 coupled with the guide wire hub 24, and the film 101 (a middle portion) forming a portion between the first end portion 98 and the second end portion 100.

The first end portion 98 is a member forming one end portion of the force transmission member 94. The first end portion 98 is positioned close to the distal end side with respect to the support rod 96. The first end portion 98 in an illustrated example is formed in an elongated shape extending in an upper-to-lower direction, but may be in an optional shape.

The first end portion 98 is disengageably coupled with the second relay cylinder 66 through a coupling mechanism 102. The coupling mechanism 102 is configured such that when the second relay cylinder 66 moves forward with respect to the housing 14, the first end portion 98 is disengaged from the second relay cylinder 66 by action of force exceeding coupling retention force between the first end portion 98 and the protector 26 on the coupling mechanism 102 after the distal end of the guide wire 22 has been housed in the inner needle 12 by retraction of the guide wire hub 24 with respect to the housing 14.

Figure 7:
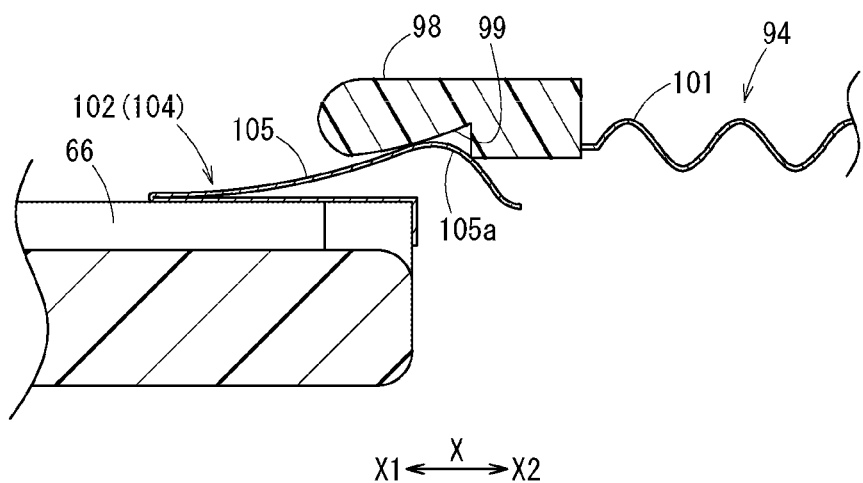
FIG. 7 is a view for describing a structure of a coupling portion between the protector and a force transmission member.

In the case of the illustrated example, the coupling mechanism 102 is a plate spring 104. As illustrated in FIG. 7, the plate spring 104 has an elastically-deformable elastic piece 105, and an engagement groove 99 is formed close to the plate spring 104 at the first end portion 98. In the initial state of the catheter assembly 10A, the elastic piece 105 of the plate spring 104 engages with the engagement groove 99 of the first end portion 98.

Coupling between the first end portion 98 and the second relay cylinder 66 is maintained by elastic force of the plate spring 104 until the distal end portion of the guide wire 22 is housed in the inner needle 12 by pulling back of the guide wire 22. When force exceeding the elastic force of the plate spring 104 acts on the plate spring 104 after the distal end portion of the guide wire 22 has been housed in the inner needle 12, the plate spring 104 elastically deforms while moving over the engagement groove 99 of the first end portion 98, and therefore, the first end portion 98 is disengaged from the second relay cylinder 66.

Moreover, the elastic piece 105 is provided with a curved expansion 105a in a shape raised toward the first end portion 98. With such a shape, the plate spring 104 is, after the plate spring 104 and the first end portion 98 engaging with each other have been released, pushed in the proximal end direction so that the plate spring 104 and the first end portion 98 can engage with each other again. Thus, even after the guide wire 22 has been pulled into the inner needle 12 in association with forward movement of the catheter member 19 (after activation of a guide wire pull-in mechanism), the catheter member 19 can be retracted for re-engagement between the plate spring 104 and the first end portion 98, and a state before activation of the guide wire pull-in mechanism can be brought. Thus, even if insertion of the catheter 16 is failed, the state before forward movement of the guide wire 22 can be restored by retraction of the catheter member 19. Consequently, the user can perform again the operation of inserting the guide wire 22 into the blood vessel and the operation of inserting the catheter member 19 into the blood vessel along the guide wire 22. In this case, the guide wire pull-in mechanism can be normally activated.

Note that the elastic piece 105 of the plate spring 104 may be, without providing the curved expansion 105a, configured to engage with the first end portion 98 at a free end portion inclined toward the first end portion 98.

Figure 8:
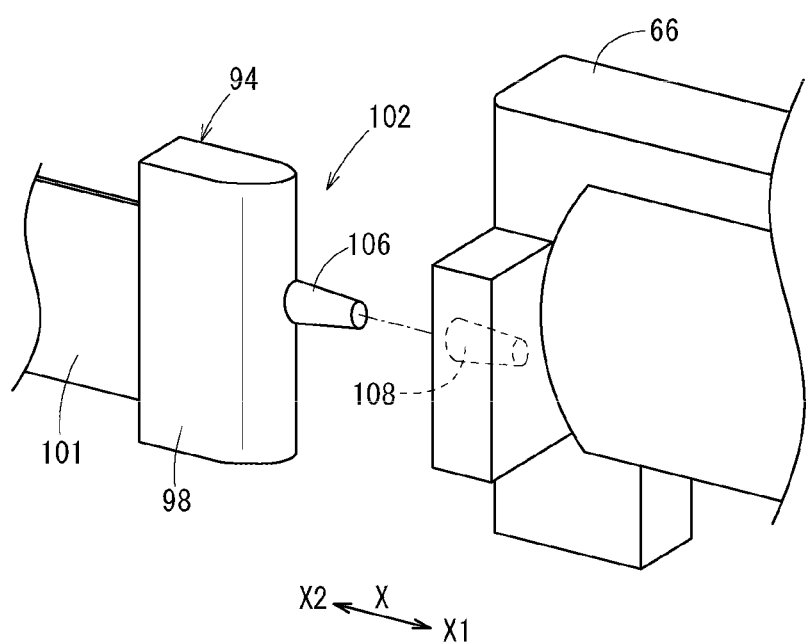
FIG. 8 is a view for describing a structure of a variation of the coupling portion between the protector and the force transmission member.

As illustrated in FIG. 8, a coupling mechanism 102 of a variation may include a fitting pin 106 provided at the first end portion 98, and a fitting hole 108 provided at the second relay cylinder 66 (the housing 14), and the fitting pin 106 may be fitted into the fitting hole 108 in the initial state of the catheter assembly 10A. In this case, coupling between the first end portion 98 and the second relay cylinder 66 is maintained by fitting force until the distal end portion of the guide wire 22 is housed in the inner needle 12 by pulling back of the guide wire 22. When force exceeding the fitting force acts on the fitting pin 106 and the fitting hole 108 after the distal end portion of the guide wire 22 has been housed in the inner needle 12, the fitting pin 106 is detached from the fitting hole 108, and therefore, the first end portion 98 is disengaged from the second relay cylinder 66. Note that the fitting hole 108 may be provided at the first end portion 98, and the fitting pin 106 may be provided at the second relay cylinder 66.

In FIG. 6, the second end portion 100 is a member forming the other end portion of the force transmission member 94, and is held at a fixing groove 110 formed at a proximal end portion of the guide wire hub 24. The second end portion 100 of the illustrated example is formed in an elongated shape extending in the upper-to-lower direction, but may be in an optional shape.

The film 101 connecting the first end portion 98 and the second end portion 100 is thin, and exhibits easily-bendable flexibility. However, the film 101 is preferably made of a material exhibiting substantially no elasticity so that the guide wire hub 24 can be pulled and retracted in the proximal end direction in association with forward movement of the protector 26.

In the initial state of the catheter assembly 10A, the film 101 is loosened. That is, the film 101 is not in a stretched state, and is sagging in a wave shape. In this case, the film 101 is at least loosened to such an extent that forward movement of the guide wire hub 24 with respect to the housing 14 is allowed to cause a predetermined length of the distal end of the guide wire 22 to protrude from the needle tip 12a of the inner needle 12.

In the present embodiment, the film 101 is, in a state in which a width direction thereof is in the upper-to-lower direction, disposed along an inner side wall surface of the housing 14 between a side surface of the guide wire hub 24 and the side wall of the housing 14. With such a layout, the force transmission member 94 can be efficiently disposed with space saving in the housing 14.

Next, features and advantageous effects of the catheter assembly 10A configured as described above will be described.

In the puncturing operation of puncturing the skin of the patient with the catheter assembly 10A in the initial state illustrated in FIG. 1, the user (the doctor, the nurse, etc.) grips the housing 14. Then, the skin is, toward the puncturing target blood vessel, punctured with a distal end portion of the catheter assembly 10A (a distal end portion of the catheter 16 into which the inner needle 12 is inserted) pressing against the patient. In this manner, the skin is punctured with the distal end portions of the inner needle 12 and the catheter 16.

Next, in the state in which the skin is punctured with the distal end portions of the inner needle 12 and the catheter 16, the user holds the position of the housing 14 while moving the guide wire hub 24 forward with respect to the housing 14. Specifically, in the case of the present embodiment, the guide wire hub 24 is moved forward as illustrated in FIG. 2 with a finger contacting a distal end portion of the guide wire hub 24.

In association with forward movement of the guide wire hub 24 with respect to the housing 14, the guide wire 22 fixed to the guide wire hub 24 is also moved in the distal end direction. Thus, the predetermined length of the guide wire 22 protrudes from the distal end opening 30a of the inner needle 12. In association with movement of the guide wire 22 in the distal end direction and protrusion of the guide wire 22 from the distal end opening 30a, the guide wire 22 is inserted into the blood vessel.

The distal end portion of the guide wire 22 is inserted to a target position in the blood vessel, and subsequently, the user fixes the position of the housing 14 while gripping the upper operation portion 56 of the catheter operation member 20 to move the catheter member 19 (the catheter 16 and the catheter hub 18) forward. Thus, the catheter 16 is inserted to the target position in the blood vessel. In this state, the catheter 16 moves forward in the blood vessel along an outer surface of the guide wire 22 inserted into the blood vessel in advance, i.e., moves forward following the guide wire 22.

Note that when the catheter operation member 20 is moved forward, the catheter operation member 20 is, about the connection protrusions 50 (see FIG. 4) as the point of support, lifted diagonally with respect to the catheter hub 18, and therefore, the catheter 16 can be inserted into the blood vessel without difficulty.

Next, the user holds the positions of the catheter operation member 20 and the catheter member 19 while pulling the housing 14 in the proximal end direction. In this manner, the catheter member 19 and the catheter operation member 20 are fully out of the housing 14, and the inner needle 12 fixed to the housing 14 is removed from the catheter 16.

Upon forward movement of the catheter hub 18 for inserting the catheter 16 into the blood vessel and retraction of the housing 14 for removing the inner needle 12 from the catheter 16, the protector 26 is extended while moving forward with respect to the housing 14. Specifically, the outer cylinder 62, the first relay cylinder 64, and the second relay cylinder 66 shift in the axial direction while the second relay cylinder 66 is moving forward with respect to the housing 14.

In a state in which the protector 26 is extended to the maximum extent as illustrated in FIG. 3, a large portion of the inner needle 12 including the needle tip 12a is housed in the protector 26. In this state, the block member 70 (see FIG. 5) blocks a needle insertion path in the inner cylinder 60 in association with movement of the needle tip 12a to the proximal end side with respect to the block member 70, and in this manner, re-protrusion of the inner needle 12 from the distal end of the protector 26 is inhibited.

Moreover, when the housing 14 is further pulled in the proximal end direction from the state in which the protector 26 is extended to the maximum extent, the catheter hub 18 and the protector 26 (the inner cylinder 60 in the present embodiment) coupled (engaging, fitting, etc.) together are released. Thus, as illustrated in FIG. 3, the protector 26 is separated from the catheter hub 18.

After the inner needle 12 has been removed from the catheter 16, the catheter operation member 20 may be detached from the catheter hub 18. Note that after the inner needle 12 has been removed from the catheter 16, the catheter operation member 20 may remain attached to the catheter hub 18.

Next, the not-shown fluid transfusion tube connector is connected to the proximal end side of the catheter member 19 from which the inner needle 12 has been removed, and the transfusion material (the medical solution) is administered to the patient through the fluid transfusion tube.

In use of the catheter assembly 10A described above, the movement mechanism 92A acts as follows.

Figure 9A:
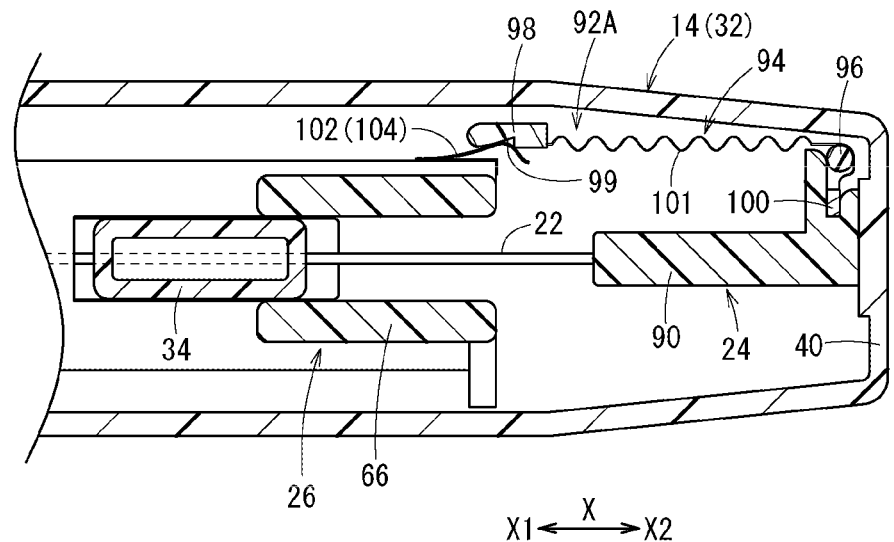
FIG. 9A is a first view for describing action of the movement mechanism of the catheter assembly illustrated in FIG. 1.

As illustrated in FIG. 9A, in the initial state of the catheter assembly 10A, the catheter hub 18 is at the most proximal position (an initial/retracted position) in a movable area, and the film 101 of the force transmission member 94 is loosened. From this state, when the guide wire hub 24 is moved forward such that the predetermined length of the distal end of the guide wire 22 protrudes from the needle tip 12a of the inner needle 12 as described above, the wire holding portion 90 comes into contact with the needle holding portion 34 as illustrated in FIG. 9B, and therefore, forward movement of the guide wire hub 24 is stopped at the most distal position (a move-out position) in the movable area.

Figure 9B:
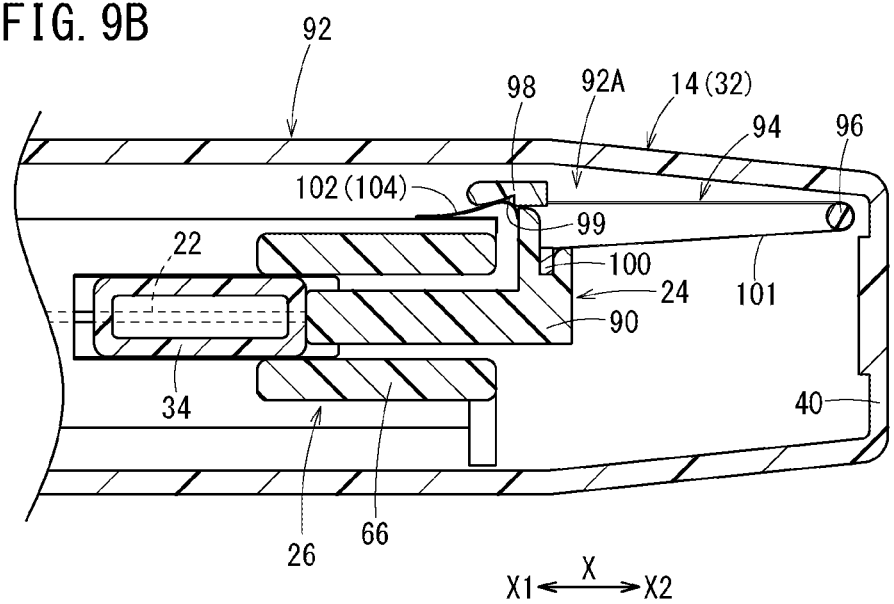
FIG. 9B is a second view for describing action of the movement mechanism of the catheter assembly illustrated in FIG. 1.

In FIG. 9B, the guide wire hub 24 is at the move-out position, and the film 101 is stretched. Note that in the state in which the guide wire hub 24 is at the move-out position, the film 101 may be slightly loosened to such an extent that retraction of the guide wire hub 24 by pulling of the force transmission member 94 as described later is not interfered.

As described above, in the initial state (FIG. 9A) of the catheter assembly 10A, the film 101 exhibits sufficient looseness for allowing forward movement of the guide wire hub 24 with respect to the housing 14. Thus, forward movement of the guide wire hub 24 is not interfered by the force transmission member 94, and the guide wire 22 can be inserted into the blood vessel without difficulty.

Figure 10A:
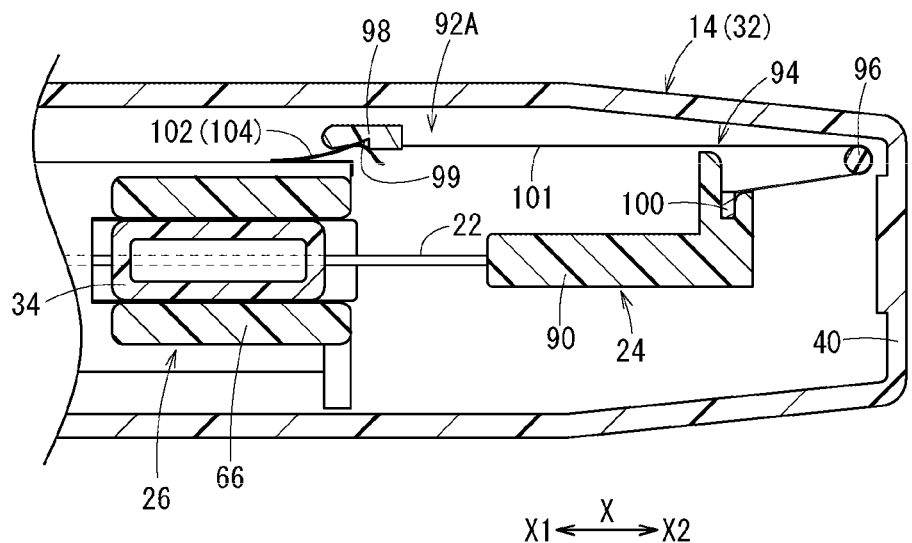
FIG. 10A is a third view for describing action of the movement mechanism of the catheter assembly illustrated in FIG. 1.

Upon forward movement of the catheter hub 18 for inserting the catheter 16 into the blood vessel or retraction of the housing 14 for removing the inner needle 12 from the catheter 16, the protector 26 is pulled in the distal end direction by the catheter hub 18. Thus, as illustrated in FIG. 10A, the protector 26 (specifically, the second relay cylinder 66) moves forward with respect to the housing 14. Note that in FIG. 10A, the second relay cylinder 66 is in the middle of forward movement.

Figure 10B:
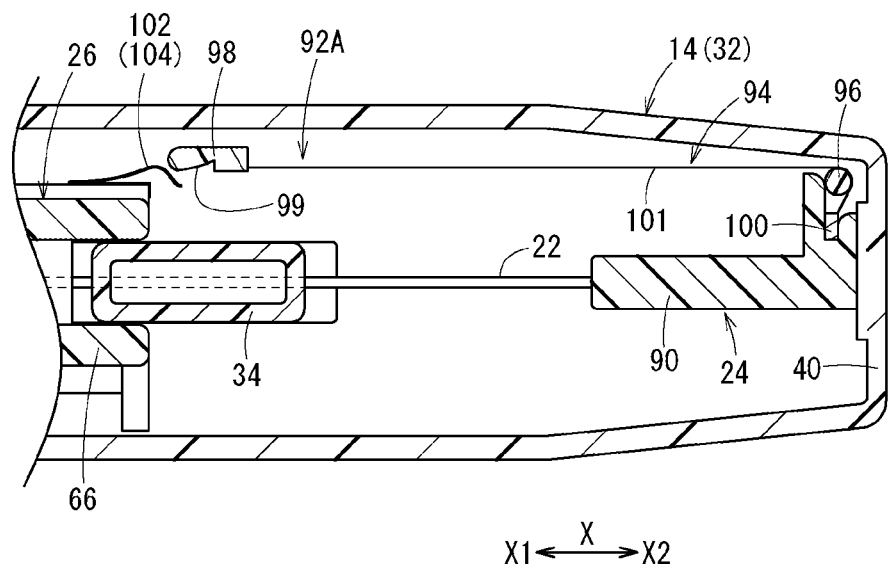
FIG. 10B is a fourth view for describing action of the movement mechanism of the catheter assembly illustrated in FIG. 1.

In association with forward movement of the second relay cylinder 66, the first end portion 98 coupled with the second relay cylinder 66 through the coupling mechanism 102 (the plate spring 104) also moves forward. As a result, the guide wire hub 24 is pulled in the proximal end direction by the force transmission member 94, and accordingly, the guide wire hub 24 is retracted. Then, as illustrated in FIG. 10B, the guide wire hub 24 is stopped at the initial position (the retracted position) by contact with the back wall 40 of the housing 14. In this manner, the guide wire 22 is retracted with respect to the inner needle 12, and the distal end of the guide wire 22 is housed in the inner needle 12 (see FIG. 3).

Meanwhile, when retraction of the guide wire hub 24 is stopped, retraction of the second end portion 100 connected to the first end portion 98 through the film 101 is also stopped. Thus, the plate spring 104 is detached from the first end portion 98 by action of force exceeding coupling retention force between the first end portion 98 and the second relay cylinder 66 on the plate spring 104, and the second relay cylinder 66 continuously moves forward. As described above, forward movement of the second relay cylinder 66 with respect to the housing 14 is not interfered by the force transmission member 94, and therefore, the inner needle 12 can be protected by the protector 26 without difficulty.

Note that the protector 26 does not necessarily have a telescopic structure including a combination of the cylindrical bodies, and may be configured such that the protector 26 also moves forward with respect to the housing 14 at the same time as forward movement of the catheter hub 18 with respect to the housing 14. In this case, the film 101 may be loosened with the guide wire hub 24 being at the move-out position. Thus, the guide wire hub 24 can be retracted after the catheter 16 has been inserted into the blood vessel along the outer surface of the guide wire 22.

As described above, according to the catheter assembly 10A, when the catheter hub 18 is moved forward with respect to the housing 14 (the needle hub) for inserting the catheter 16 into the blood vessel along the outer surface of the guide wire 22, the guide wire hub 24 is automatically pulled back under action of the movement mechanism 92A, and the distal end of the guide wire 22 is housed in the inner needle 12. This can inhibit spattering of blood adhering to the guide wire 22.

In the case of the present embodiment, when the catheter hub 18 moves forward with respect to the housing 14, the movement mechanism 92A converts the force for forward moving, with respect to the housing 14, the protector 26 following the catheter hub 18 into the force for retracting the guide wire hub 24 with respect to the housing 14. With this configuration, the guide wire 22 can be reliably pulled back by means of movement of the protector 26 following the catheter hub 18.

In the case of the present embodiment, the force transmission member 94 has the first end portion 98 coupled with the protector 26, the second end portion 100 coupled with the guide wire hub 24, and the film 101 hooked on the support rod 96 provided at the housing 14. With this configuration, when the protector 26 moves forward with respect to the housing 14, the first end portion 98 coupled with the protector 26 moves forward while the second end portion 100 coupled with the guide wire hub 24 is retracted. Thus, the force for moving the protector 26 forward with respect to the housing 14 can be efficiently converted into the force for retracting the guide wire hub 24 with respect to the housing 14.

In the case of the present embodiment, when the catheter 16 is moved forward with respect to the inner needle 12 from the state in which the predetermined length of the distal end portion of the guide wire 22 protrudes from the distal end of the inner needle 12, the movement mechanism 92A moves the catheter 16 forward with respect to the guide wire 22 by a predetermined distance, and then, retracts the guide wire hub 24 with respect to the housing 14. With this configuration, when the catheter 16 is inserted into the blood vessel, the guide wire 22 begins retracting after the catheter 16 has been inserted into the blood vessel along the outer surface of the guide wire 22. Thus, the guide wire 22 can be pulled back in association with the operation of moving out the catheter 16 without interference of a guide function of the guide wire 22.

Specifically in the case of the present embodiment, the mechanism configured to retract the guide wire hub 24 with respect to the housing 14 after the catheter 16 has moved forward with respect to the guide wire 22 by the predetermined distance is realized by the protector 26 having the telescopic structure. That is, when the catheter 16 is moved forward with respect to the inner needle 12, the inner cylinder 60, the outer cylinder 62, and the first relay cylinder 64 of the protector 26 move forward with respect to the second relay cylinder 66 with the second relay cylinder 66 being stopped at the housing 14. Thus, the second relay cylinder 66 begins moving forward with respect to the housing 14 at timing later than the beginning of forward movement of the catheter 16. As a result, the timing of retracting the guide wire hub 24 with respect to the housing 14 under action of the force transmission mechanism is timing after the catheter 16 has moved forward with respect to the guide wire 22 by the predetermined distance.

Note that in the present embodiment, the second relay cylinder 66 of the protector 26 has been described as an example of the movable member configured to move forward with respect to the housing 14 in association with the forward movement of the catheter hub 18 with respect to the housing 14 forming the needle hub. However, the movable member may be other members than the protector 26.

Second Embodiment

In a catheter assembly 10B of the second embodiment illustrated in FIG. 11, a movement mechanism 92B is coupled with a catheter hub 18 and a guide wire hub 24, and is configured to convert the force for moving the catheter hub 18 forward with respect to a housing 14 into the force for retracting the guide wire hub 24 with respect to the housing 14.

In the present embodiment, the movement mechanism 92B includes a force transmitter configured to transmit force to the guide wire hub 24 in association with movement of the catheter hub 18, and a force direction changer configured to change the direction of force of the force transmitter. In the present embodiment, the force transmitter is a force transmission member 112, and more specifically, a film 118. The force direction changer is a support rod 96 as a support portion. The force transmitter transmits, to the guide wire hub 24, force accompanied by movement in the direction of moving the catheter hub 18 forward with respect to the housing 14. In this state, the direction of force of forward movement at a portion of the force transmitter is changed by the force direction changer. The force in the changed direction is transmitted to other portions of the force transmitter. The force transmitted to the other portions of the force transmitter retracts the guide wire hub 24.

Specifically, the movement mechanism 92B includes the force transmission member 112 exhibiting flexibility, and the support rod 96 provided at the housing 14. The force transmission member 112 has a first end portion 114 coupled with the catheter hub 18, a second end portion 116 (see FIG. 12) coupled with the guide wire hub 24, and the film 118 (a middle portion) forming a portion between the first end portion 114 and the second end portion 116. The film 118 is hooked on the support rod 96 on the proximal end side (the proximal end side of the housing 14) with respect to a coupling position between the first end portion 114 and a protector 26.

The first end portion 114 is disengageably coupled with the catheter hub 18. In the case of the present embodiment, the first end portion 114 has a C-shaped fitting recessed portion 120, and the fitting recessed portion 120 is fitted onto an outer peripheral portion of the catheter hub 18. When an inner needle 12 is removed from a catheter 16, a user pulls the first end portion 114 outward so that the first end portion 114 can be detached from the catheter hub 18.

The structure of disengageably coupling the first end portion 114 with the catheter hub 18 is not limited to the above-described structure. For example, a fitting pin may be provided at one of the first end portion 114 and the catheter hub 18, and a fitting hole may be provided at the other one of the first end portion 114 and the catheter hub 18. By fitting of the fitting pin into the fitting hole, the first end portion 114 may be disengageably coupled with the catheter hub 18.

Figure 13:
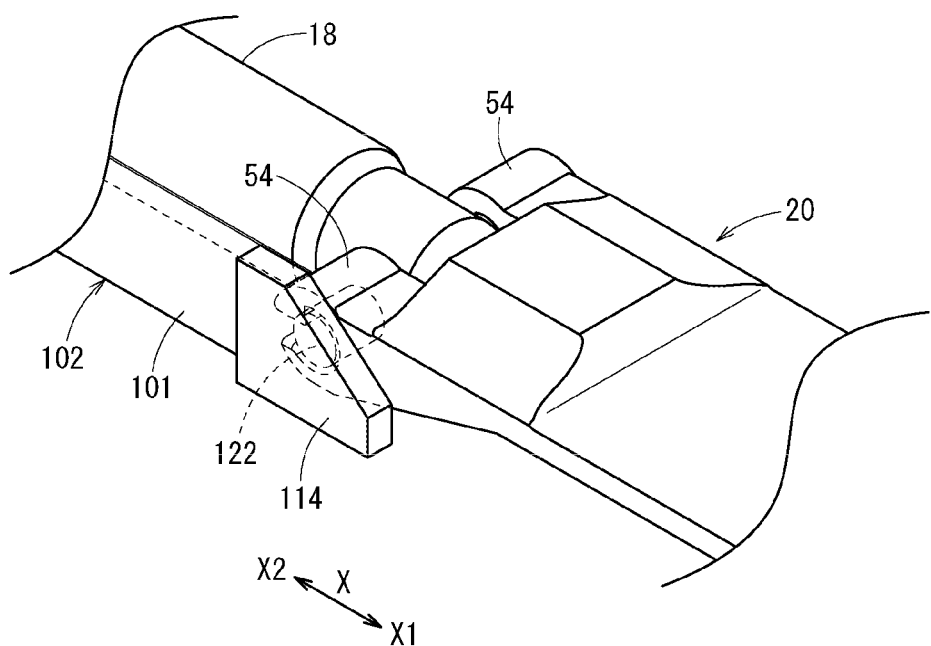
FIG. 13 is a view for describing a structure of a variation of a coupling portion between a catheter operation member and a force transmission member.

As illustrated in FIG. 13, the first end portion 114 may be coupled with a catheter operation member 20. In this case, the first end portion 114 has fitting pins 122, and each fitting pin 122 is fitted in a corresponding one of connection pieces 54 provided at a proximal end portion of the catheter operation member 20.

Figure 12:
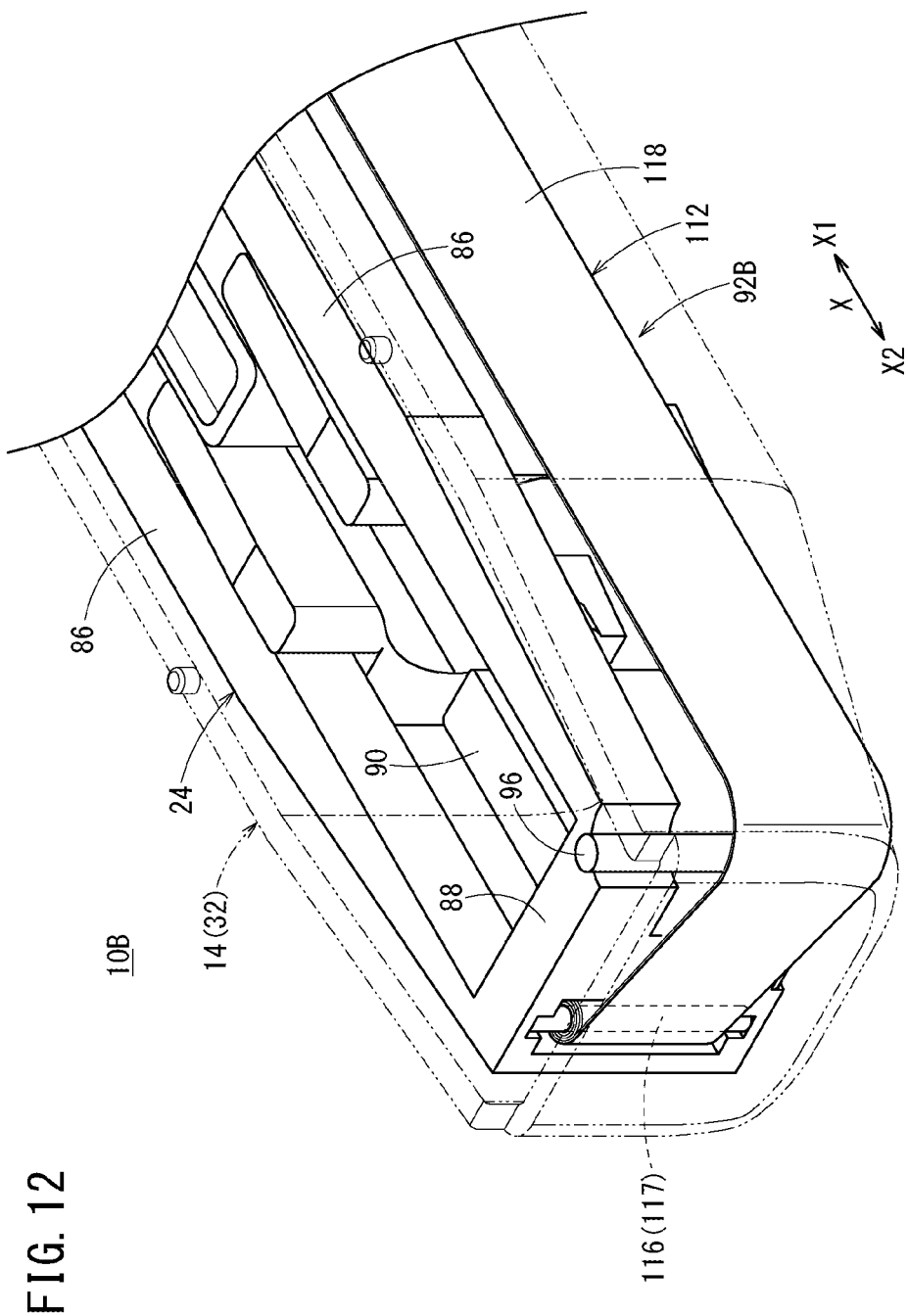
FIG. 12 is a view for describing a structure of a movement mechanism of the catheter assembly illustrated in FIG. 11.

In the case of the present embodiment, the second end portion 116 is a winding shaft 117 rotatably coupled with a proximal end portion of the guide wire hub 24, as illustrated in FIG. 12. In an initial state of the catheter assembly 10B, a portion of the film 118 is wound around the winding shaft 117. The winding shaft 117 is disposed such that an axial direction thereof is along an upper-to-lower direction. A width direction of the film 118, the axial direction of the winding shaft 117, and an axial direction of the support rod 96 are parallel to each other.

In the initial state of the catheter assembly 10B, the first end portion 114 is on the distal end side with respect to the position of the first end portion 98 in the first embodiment. Thus, the length of the film 118 is longer than the length of the film 101 in the second embodiment.

In the initial state of the catheter assembly 10B, the length (the winding length) of a portion of the film 118 wound around the winding shaft 117 is a sufficient length for allowing the guide wire hub 24 to move forward with respect to the housing 14 to protrude a predetermined length of a distal end of a guide wire 22 from a distal end of the inner needle 12. That is, the film 118 has a length allowance for allowing forward movement of the guide wire hub 24 with respect to the housing 14. Note that instead of or in addition to winding around the winding shaft 117, the film 118 may be folded or loosened in a wave shape such that the length allowance for allowing forward movement of the guide wire hub 24 with respect to the housing 14 is ensured.

The method for using the catheter assembly 10B is similar to the method for using the catheter assembly 10A of the first embodiment as described above. That is, in use of the catheter assembly 10B, the user operates the guide wire hub 24 in the distal end direction after a patient's skin has been punctured with a distal end portion of the catheter assembly 10B in the initial state illustrated in FIG. 11, thereby protruding the predetermined length of the guide wire 22 from the distal end of the inner needle 12. Next, the user moves the catheter operation member 20 forward to insert the catheter 16 to a target position in a blood vessel. Next, the user pulls the housing 14 in the proximal end direction to remove the inner needle 12 from the catheter 16.

In such use of the catheter assembly 10B, the movement mechanism 92B configured as described above acts as follows.

As illustrated in FIG. 14A, in the initial state of the catheter assembly 10B, the catheter hub 18 is at the most proximal position (an initial/retracted position) in a movable area, and a portion of the film 118 of the force transmission member 112 is wound around the winding shaft 117. From this state, the guide wire hub 24 is moved forward to protrude the predetermined length of the distal end of the guide wire 22 from the distal end of the inner needle 12 as described above.

Accordingly, a distal end surface of a wire holding portion 90 comes into contact with a needle holding portion 34 such that the guide wire hub 24 is stopped at the most distal position (a move-out position) in the movable area, as illustrated in FIG. 14B. In association with forward movement of the guide wire hub 24, the film 118 is wound back from the winding shaft 117. In FIG. 14B, the film 118 is stretched.

As described above, in the initial state (FIG. 14A) of the catheter assembly 10B, the film 118 is partially wound around the winding shaft 117, and therefore, has a sufficient length allowance for allowing forward movement of the guide wire hub 24 with respect to the housing 14. Thus, forward movement of the guide wire hub 24 is not interfered by the force transmission member 112, and the guide wire 22 can be inserted into the blood vessel without difficulty.

Figure 15A:
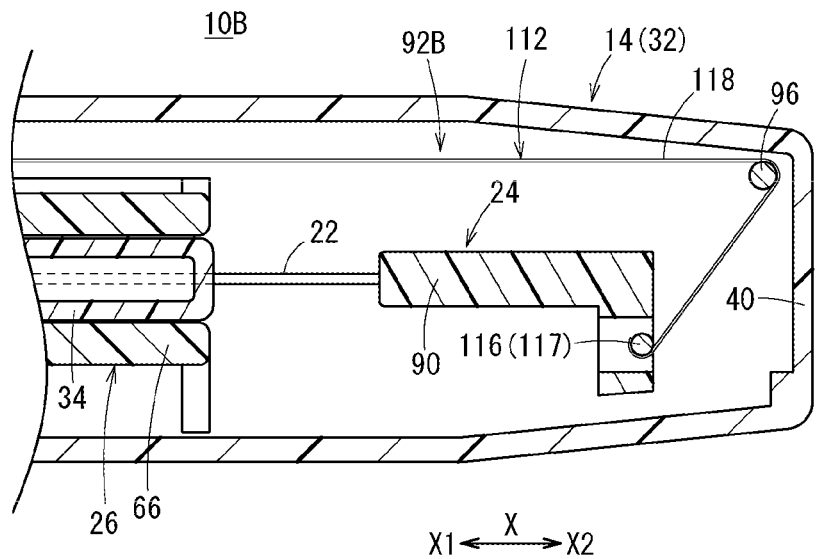
FIG. 15A is a third view for describing action of the movement mechanism of the catheter assembly illustrated in FIG. 11.

Upon forward movement of the catheter hub 18 for inserting the catheter 16 into the blood vessel, the first end portion 114 coupled with the catheter hub 18 also moves forward. Thus, as illustrated in FIG. 15A, the guide wire hub 24 is pulled in the proximal end direction by the force transmission member 112, and accordingly, the guide wire 22 is retracted. In this state, in a case where there is no length allowance of the film 118 in the state of FIG. 14B (a case where the film 118 is stretched), the guide wire 22 is retraced at the same time as the beginning of forward movement of the catheter hub 18. Note that in FIG. 15A, the state of the guide wire hub 24 etc. in the middle of forward movement of the catheter hub 18 is illustrated.

Figure 15B:
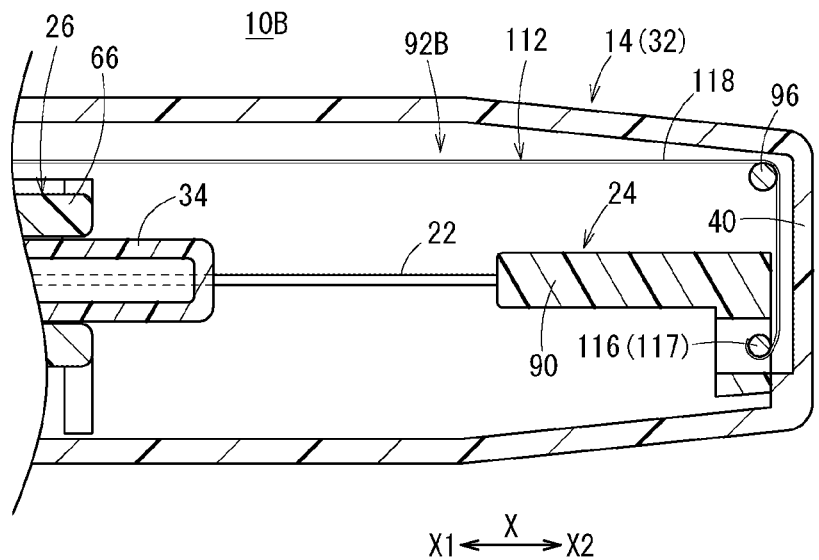
FIG. 15B is a fourth view for describing action of the movement mechanism of the catheter assembly illustrated in FIG. 11.

As illustrated in FIG. 15B, the guide wire hub 24 comes into contact with a back wall 40 of the housing 14, and therefore, is stopped at the initial position (the retracted position). In this state, the guide wire 22 is retracted with respect to the inner needle 12, and the distal end of the guide wire 22 is housed in the inner needle 12. This can inhibit spattering of blood adhering to the guide wire 22 after removal of the inner needle 12 from the catheter 16.

Note that in the state of FIG. 14B, the film 118 may have a length allowance exceeding a length exactly required for allowing forward movement of the guide wire hub 24 with respect to the housing 14. In this case, the length allowance of the film 118 can be provided by winding, wave-shaped looseness, folding, etc. The timing of beginning retraction of the guide wire 22 can be set according to the size of the length allowance of the film 118.

For example, in the state (FIG. 14B) in which the guide wire hub 24 is positioned at the move-out position, the length allowance of the film 118 may be set such that the guide wire 22 begins retracting after the catheter 16 has moved forward along the guide wire 22 by a predetermined distance. Thus, when the catheter 16 is inserted into the blood vessel, the guide wire 22 begins retracting after the catheter 16 has been inserted into the blood vessel along an outer surface of the guide wire 22. Thus, the guide wire 22 can be pulled back in association with the operation of moving out the catheter 16 without interference of a guide function of the guide wire 22.

When the inner needle 12 is removed from the catheter 16, the first end portion 114 is detached from the catheter hub 18. Thus, the force transmission member 112 is separated from the catheter hub 18. Note that in the case (FIG. 13) of coupling the first end portion 114 with the catheter operation member 20, the catheter operation member 20 is, together with the first end portion 114, detached from the catheter hub 18 so that the force transmission member 112 can be separated from the catheter hub 18.

Note that in the catheter assembly 10B, the protector 26 is not necessarily provided.

Of the second embodiment, portions common to the first embodiment provide features and advantageous effects identical or similar to those of the first embodiment.

Third Embodiment

Figure 16:
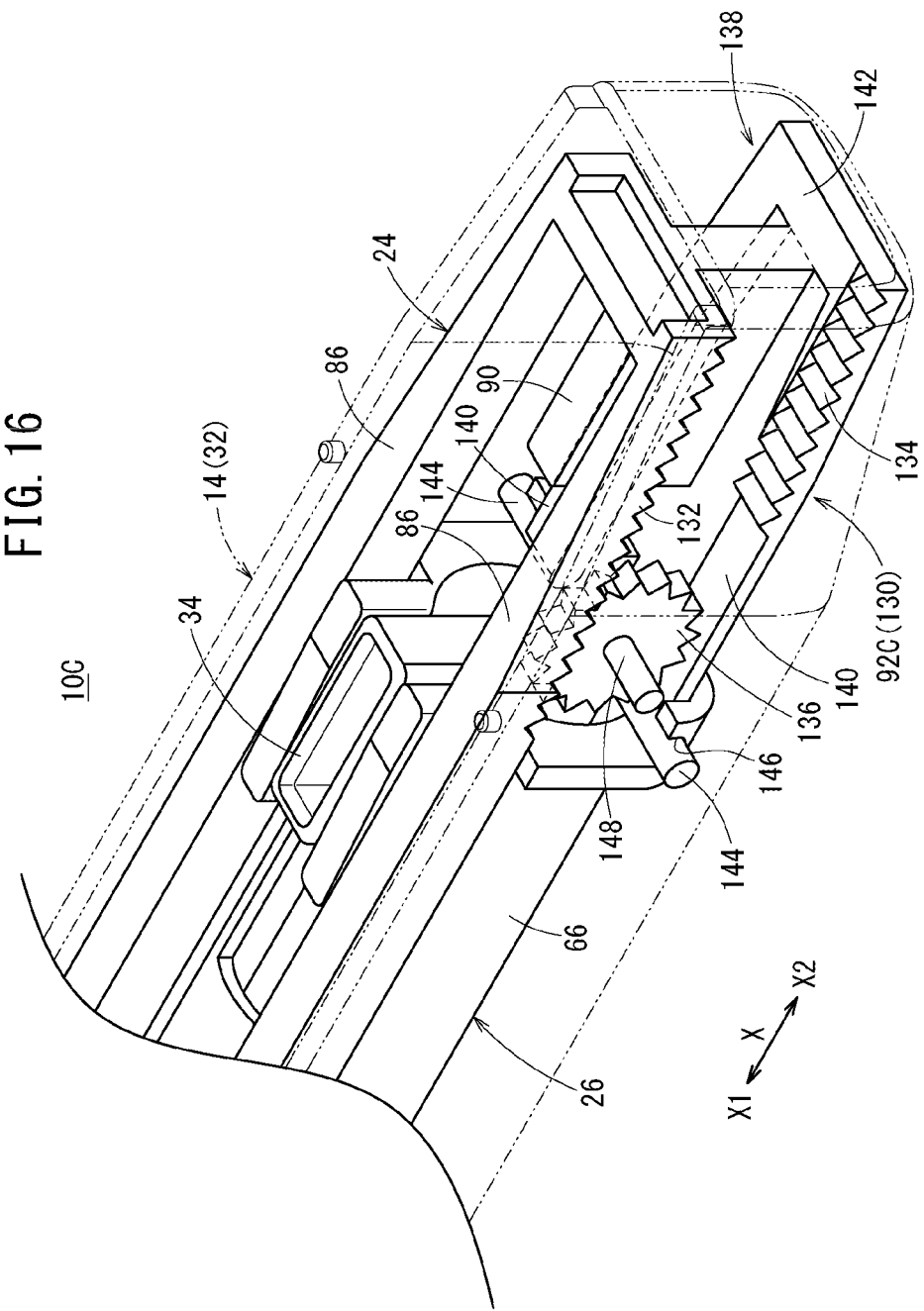
FIG. 16 is a perspective view of a main portion of a catheter assembly of a third embodiment of the present invention.

In a catheter assembly 10C of the third embodiment illustrated in FIG. 16, a movement mechanism 92C is in the form of a gear mechanism 130 configured to convert, through a gear, forward movement of a protector 26 with respect to a housing 14 into retraction movement of a guide wire hub 24 with respect to the housing 14.

In the present embodiment, the movement mechanism 92C includes a force transmitter configured to transmit force to the guide wire hub 24 in association with movement of a catheter hub 18, and a force direction changer configured to change the direction of force of the force transmitter. In the present embodiment, the force transmitter corresponds to a first rack portion 132 provided at the guide wire hub 24 and a second rack portion 134 provided at a second relay cylinder. The force direction changer is a gear wheel 136. The force transmitter transmits, to the guide wire hub 24, force accompanied by movement in the direction of moving the catheter hub 18 forward with respect to the housing 14. In this state, the direction of force of forward movement at a portion of the force transmitter is changed by the force direction changer. The force in the changed direction is transmitted to other portions of the force transmitter. The force transmitted to the other portions of the force transmitter retracts the guide wire hub 24.

The gear mechanism 130 has the first rack portion 132 configured to move together with the guide wire hub 24 upon movement of the guide wire hub 24 with respect to the housing 14, the second rack portion 134 configured to move together with the protector 26 upon movement of the protector 26 (a second relay cylinder 66) with respect to the housing 14, and the gear wheel 136 provided at the housing 14. When the protector 26 moves forward with respect to the housing 14, force of forward movement of the second rack portion 134 is transmitted to the first rack portion 132 through the gear wheel 136, and accordingly, the first rack portion 132 retracts.

In the present embodiment, the first rack portion 132 is formed along an axial direction at a proximal-end-side lower surface of one of extensions 86 of the guide wire hub 24. The first rack portion 132 may be molded integrally with the guide wire hub 24 as in an illustrated example, or may be a separate member connected to the guide wire hub 24. Note that the first rack portion 132 may be provided not only at one of the extensions 86 of the guide wire hub 24, but also at the other extension 86.

In the present embodiment, the second rack portion 134 is formed at a rack member 138 extending from a proximal end portion of the second relay cylinder 66 in the proximal end direction. The rack member 138 has a pair of arm portions 140 extending in the axial direction, and a coupling portion 142 connecting proximal ends of the arm portions 140. The rack member 138 is in a U-shape as viewed in the plane. Distal ends of the arm portions 140 are provided respectively with right and left engagement pins 144 protruding outward in a right-to-left direction, and the right and left engagement pins 144 engage respectively with right and left upwardly-opening engagement recessed portions 146 provided at a lower proximal end portion of the second relay cylinder 66. Thus, when the second relay cylinder 66 moves with respect to the housing 14 in the axial direction, the rack member 138 also moves in the axial direction together with the second relay cylinder 66. Note that the second rack portion 134 may be provided not only at one of the arm portions 140, but also at the other arm portion 140.

The second rack portion 134 is formed along the axial direction at a proximal-end-side upper surface of one of the arm portions 140. The length of the second rack portion 134 along the axial direction is shorter than the length of the first rack portion 132 along the axial direction. Note that the rack member 138 and the second relay cylinder 66 may be integrally molded. That is, the rack member 138 may be a portion of the second relay cylinder 66.

The gear wheel 136 is disposed between the first rack portion 132 and the rack member 138, and is rotatably supported by a shaft portion 148 fixed to the housing 14. Note that the gear wheel 136 and the shaft portion 148 may be integrally molded, or may be fixed not to rotate relative to each other such that the shaft portion 148 is rotatably supported by the housing 14. The axis of rotation of the gear wheel 136 is perpendicular to the axial direction of the catheter assembly 10C, and in the present embodiment, is along the right-to-left direction.

The gear wheel 136 engages with the first rack portion 132 across the entirety of a movable area of the guide wire hub 24 with respect to the housing 14. In an initial state of the catheter assembly 10C, the rack member 138 is at an initial position illustrated in FIG. 16, and the second rack portion 134 does not engage with the gear wheel 136. As will be described later, the second rack portion 134 engages with the gear wheel 136 after the second rack portion 134 has moved forward with respect to the housing 14 by a predetermined distance.

The method for using the catheter assembly 10C is similar to the method for using the catheter assembly 10A of the first embodiment as described above. That is, in use of the catheter assembly 10C, a user moves the guide wire hub 24 forward with respect to the housing 14 after a patient's skin has been punctured with a distal end portion of the catheter assembly 10C in the initial state illustrated in FIG. 16, thereby protruding a predetermined length of a guide wire 22 from a distal end of an inner needle 12. Next, the user moves a catheter operation member 20 forward, thereby inserting a catheter 16 to a target position in a blood vessel. Next, the user pulls the housing 14 in the proximal end direction, thereby removing the inner needle 12 from the catheter 16.

In such use of the catheter assembly 10C, the movement mechanism 92C in the form of the gear mechanism 130 as described above acts as follows.

As illustrated in FIG. 17A, in the initial state of the catheter assembly 10C, the guide wire hub 24 is at the most proximal position (the initial/retracted position) in the movable area. From this state, the guide wire hub 24 is moved forward such that the predetermined length of a distal end of the guide wire 22 protrudes from a needle tip 12a of the inner needle 12 as described above.

Accordingly, a distal end surface of a wire holding portion 90 comes into contact with a needle holding portion 34 as illustrated in FIG. 17B, and therefore, the guide wire hub 24 is stopped at the most distal position (a move-out position) in the movable area. While the guide wire hub 24 is moving from the initial position to the move-out position, the first rack portion 132 provided at the guide wire hub 24 engages with the gear wheel 136. However, the second rack portion 134 is positioned on the proximal end side with respect to the position at which the second rack portion 134 engages with the gear wheel 136, and therefore, does not engage with the gear wheel 136. Thus, the gear wheel 136 is rotated in association with forward movement of the guide wire hub 24, but idles with respect to the second rack portion 134. Thus, forward movement of the guide wire hub 24 is not interfered by the gear mechanism 130, and the guide wire 22 can be inserted into the blood vessel without difficulty.

Figure 18A:
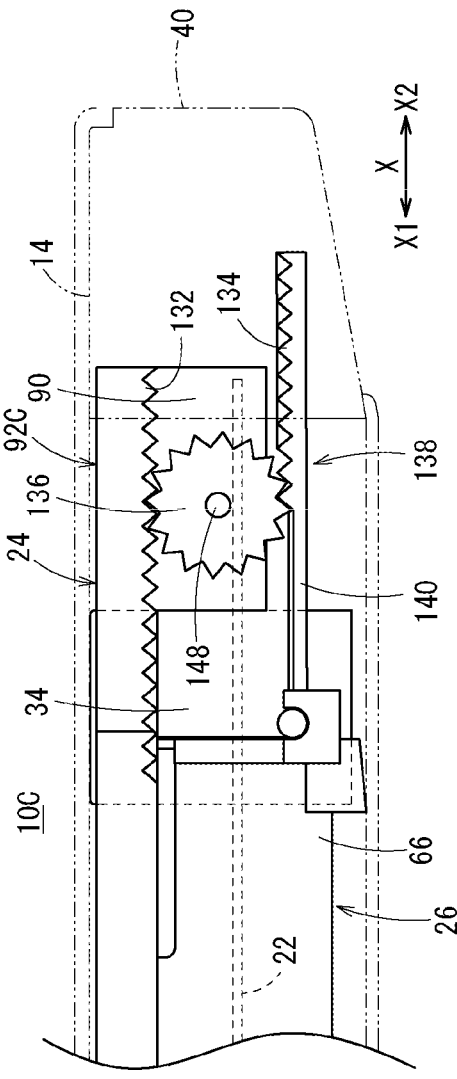
FIG. 18A is a third view for describing action of the movement mechanism of the catheter assembly illustrated in FIG. 16.

Upon forward movement of the catheter hub 18 for inserting the catheter 16 into the blood vessel or retraction of the housing 14 for removing the inner needle 12 from the catheter 16, the protector 26 is pulled in the distal end direction by the catheter hub 18, and therefore, the protector 26 (specifically, the second relay cylinder 66) moves forward with respect to the housing 14. In association with forward movement of the second relay cylinder 66, the rack member 138 coupled with the second relay cylinder 66 also moves forward with respect to the housing 14, and as illustrated in FIG. 18A, the gear wheel 136 and the second rack portion 134 begin engaging with each other at a position at which the rack member 138 has moved forward from the initial position by a predetermined distance.

Then, in this state, the gearwheel 136 engages with both of the first rack portion 132 and the second rack portion 134. Thus, in association with forward movement of the second relay cylinder 66 and the rack member 138, the gearwheel 136 is rotatably driven by the second rack portion 134, and the first rack portion 132 is driven in the proximal end direction by the rotating gear wheel 136. Accordingly, the guide wire hub 24 retracts with respect to the housing 14.

Figure 18B:
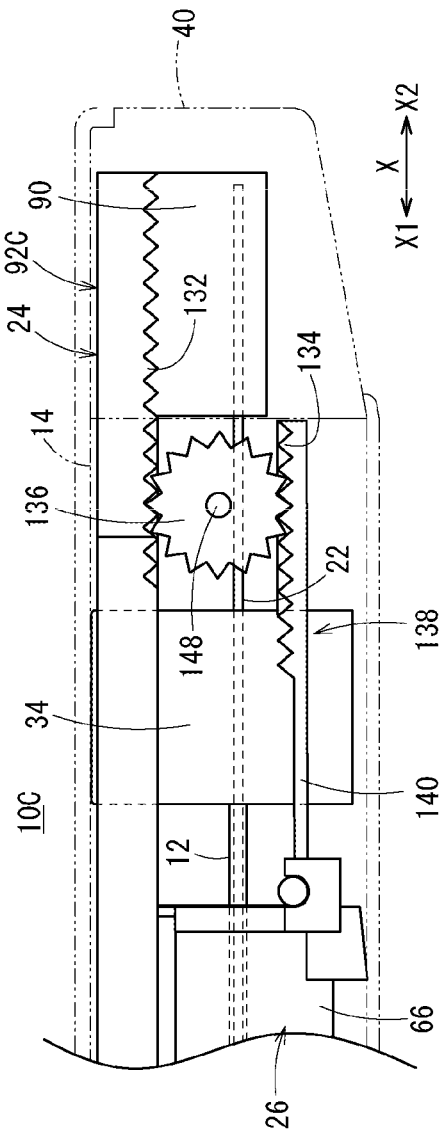
FIG. 18B is a fourth view for describing action of the movement mechanism of the catheter assembly illustrated in FIG. 16.

Then, as illustrated in FIG. 18B, the guide wire hub 24 is stopped at the initial position (the retracted position). Accordingly, the guide wire 22 retracts with respect to the inner needle 12, and the distal end of the guide wire 22 is housed in the inner needle 12. Note that the guide wire hub 24 may be stopped by contact with a back wall 40 of the housing 14.

As described above, according to the catheter assembly 10C, when the catheter hub 18 is moved forward with respect to the housing 14 (a needle hub) for inserting the catheter 16 into the blood vessel along an outer surface of the guide wire 22, the guide wire hub 24 is pulled back under action of the gear mechanism 130, and the distal end of the guide wire 22 is housed in the inner needle 12. This can inhibit spattering of blood adhering to the guide wire 22.

Moreover, in the present embodiment, the force for moving the protector 26 forward with respect to the housing 14 can be, by the gear mechanism 130, efficiently converted into the force for retracting the guide wire hub 24 with respect to the housing 14. Specifically, when the protector 26 moves forward with respect to the housing 14, the force of forward movement of the second rack portion 134 is transmitted to the first rack portion 132 through the gear wheel 136, and accordingly, the first rack portion 132 retracts. Thus, the gear mechanism 130 configured to retract the guide wire hub 24 in association with forward movement of the protector 26 can be built with a simple configuration.

In the case of the present embodiment, when the catheter 16 is moved forward with respect to the inner needle 12 from the state in which the predetermined length of a distal end portion of the guide wire 22 protrudes from the needle tip 12a, the gear mechanism 130 retracts the guide wire hub 24 with respect to the housing 14 after the catheter 16 has moved forward with respect to the guide wire 22 by a predetermined distance. With this configuration, when the catheter 16 is inserted into the blood vessel, the guide wire 22 begins retracting after the catheter 16 has been inserted into the blood vessel along the outer surface of the guide wire 22. Thus, the guide wire 22 can be pulled back in association with the operation of moving out the catheter 16 without interference of a guide function of the guide wire 22.

Moreover, in the case of the present embodiment, even after the guide wire 22 has been pulled into the inner needle 12 in association with forward movement of a catheter member 19 (after activation of a guide wire pull-in mechanism), the catheter member 19 is retracted so that a state before activation of the guide wire pull-in mechanism can be brought. Specifically, the second rack portion 134 retracts in association with retraction movement of the catheter member 19. The gear wheel 136 rotates in association with such retraction of the second rack portion 134, and the first rack portion 132 moves forward in association with such rotation of the gear wheel 136. Thus, the guide wire 22 protrudes from the distal end of the inner needle 12 again. Then, by further retraction of the catheter member 19, the second rack portion 134 moves toward the proximal end side with respect to the gear wheel 136, leading to the state before activation of the guide wire pull-in mechanism. Thus, the user can perform again the operation of inserting the catheter member 19 into the blood vessel along the guide wire 22.

Note that in the catheter assembly 10C, the gear wheel 136 may have a first gear configured to engage with the first rack portion 132, and a second gear configured to rotate together with the first gear and engage with the second rack portion 134 and having a smaller number of gear teeth than that of the first gear and a smaller diameter than that of the first gear. With this configuration, in a state in which the first gear and the first rack portion 132 engage with each other and the second gear and the second rack portion 134 engage with each other, the movement distance of the first rack portion 132 when the first rack portion 132 retracts in association with forward movement of the second rack portion 134 is longer than that of the second rack portion 134. Thus, the length of the second rack portion 134 can be shortened as compared to that in the case of using the gear wheel 136 having the single gear.

Of the third embodiment, portions common to the first embodiment provide features and advantageous effects identical or similar to those of the first embodiment.

Fourth Embodiment

Figure 19:
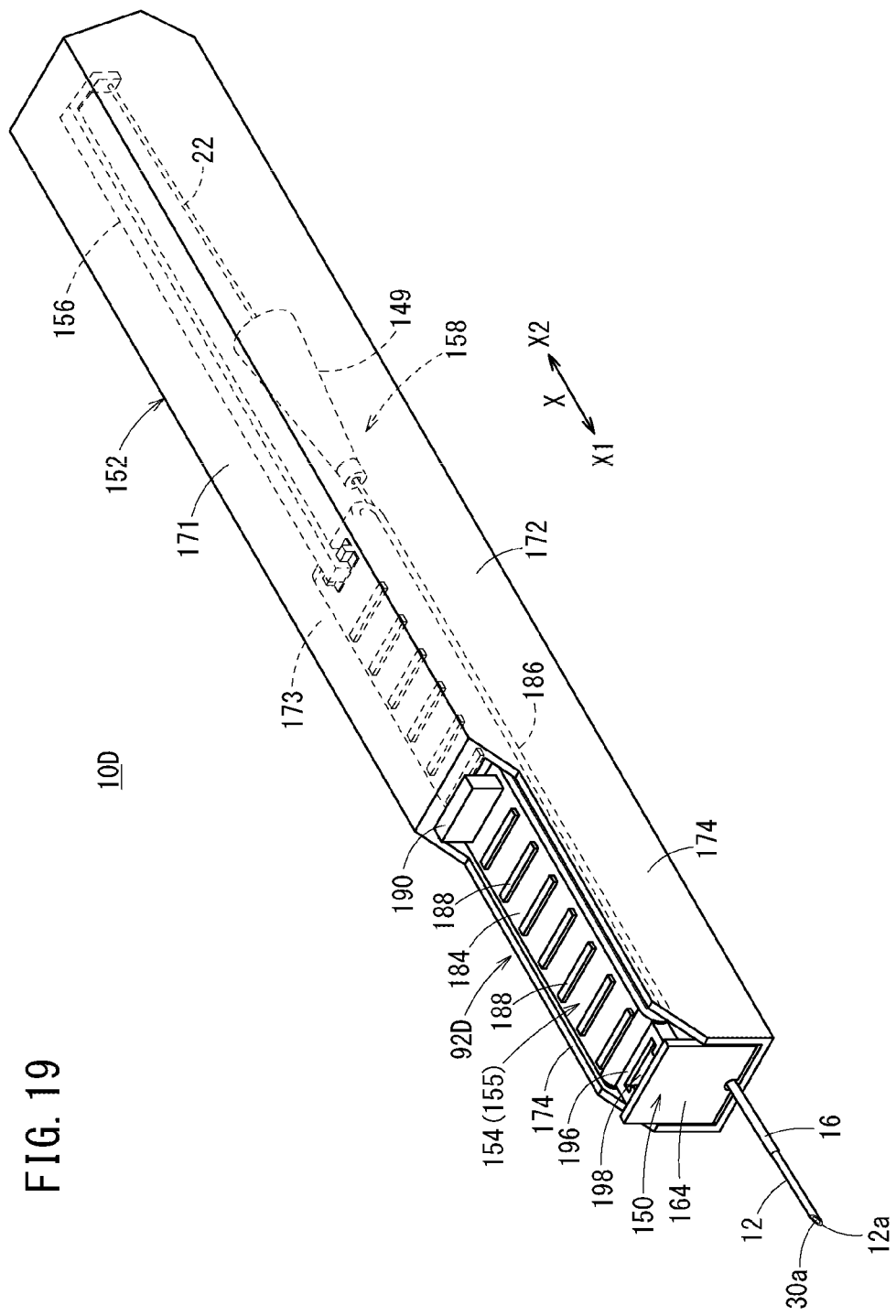
FIG. 19 is a perspective view of a catheter assembly of a fourth embodiment of the present invention.
Figure 20:
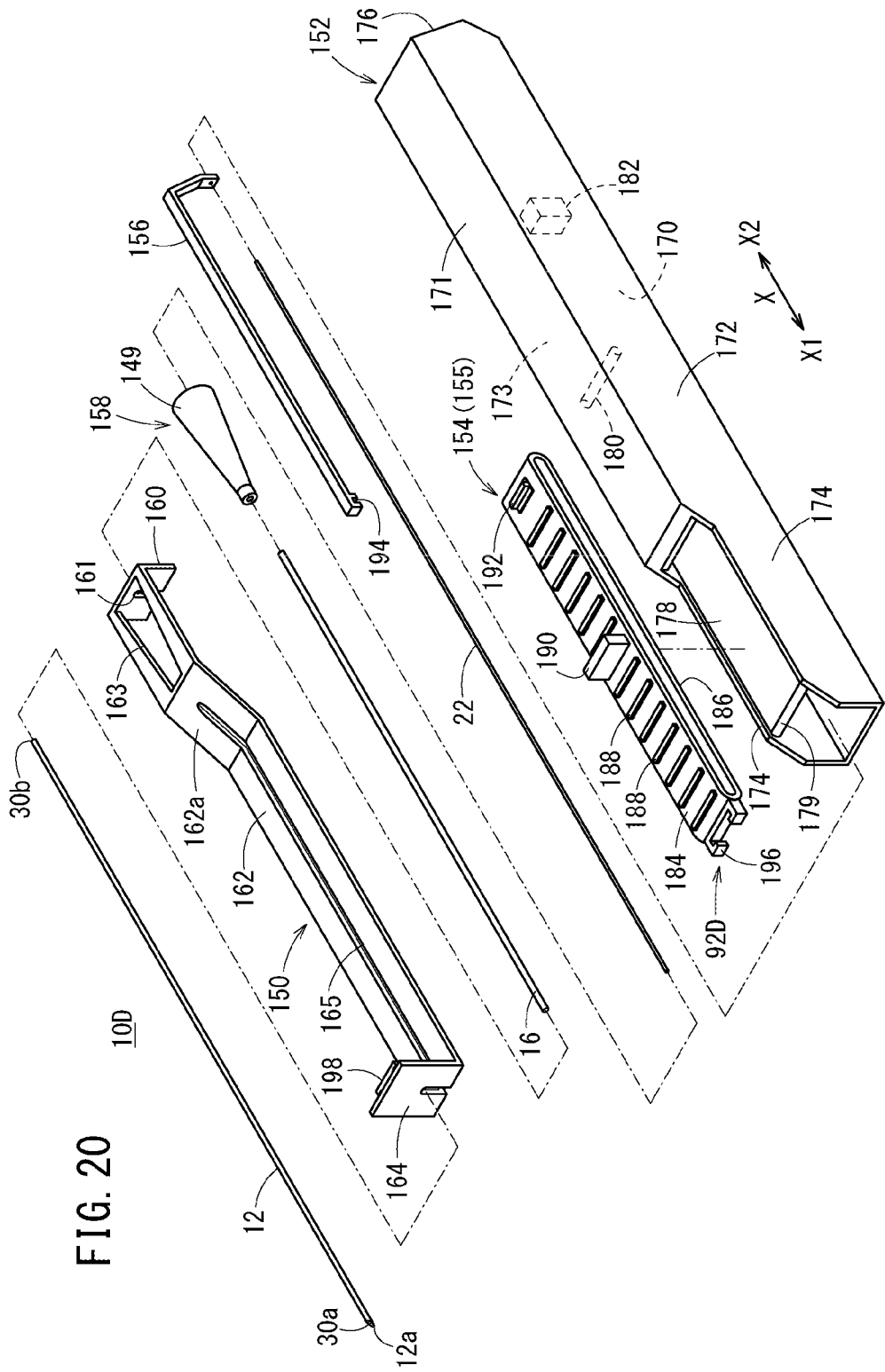
FIG. 20 is an exploded perspective view of the catheter assembly illustrated in FIG. 19.

A catheter assembly 10D of the fourth embodiment illustrated in FIGS. 19 and 20 includes a catheter 16, a catheter hub 149 fixed to the catheter 16, a catheter operation member 150 coupled with the catheter hub 149, a hollow inner needle 12 inserted into the catheter 16, a housing 152 fixed to the inner needle 12, a guide wire 22 inserted into the housing 152, a wire operation member 154 supported by the housing 152, and a connection member 156 coupled with the guide wire 22 and the wire operation member 154.

In the present embodiment, a movement mechanism includes a force transmitter configured to transmit force to a guide wire hub (the connection member 156) in association with movement of the catheter hub 149, and a force direction changer configured to change the direction of force of the force transmitter. In the present embodiment, the force transmitter corresponds to the wire operation member 154. The force direction changer includes a support plate 178 and a support pin 180 as a support portion. The force transmitter transmits, to the guide wire hub (the connection member 156), force accompanied by movement in the direction of moving the catheter hub 149 forward with respect to the housing 152. In this state, the direction of force of forward movement at a portion of the force transmitter is changed by the force direction changer. The force in the changed direction is transmitted to other portions of the force transmitter. The force transmitted to the other portions of the force transmitter retracts the guide wire hub (the connection member 156).

The catheter 16, the inner needle 12, and the guide wire 22 have the same configurations as those of the catheter 16, the inner needle 12, and the guide wire 22 in the first embodiment as described above.

The catheter hub 149 is liquid-tightly connected and fixed to a proximal end of the catheter 16. The catheter 16 and the catheter hub 149 form a catheter member 158.

The catheter operation member 150 is an operation unit configured to move the catheter 16 in the distal end direction through the catheter hub 149. In an initial state of the catheter assembly 10D, the catheter operation member 150 extends substantially along the inner needle 12 and the catheter 16. Of the catheter operation member 150, a proximal end portion engages with the catheter hub 149, and a distal end portion is exposed on the distal end side of the housing 152.

As illustrated in FIG. 20, the catheter operation member 150 has a hub contact portion 160 configured to contact a proximal end surface of the catheter hub 149, an elongated body portion 162 extending from the hub contact portion 160 in the distal end direction, and a tab 164 protruding upward from a distal end of the body portion 162.

The hub contact portion 160 is provided with a downwardly-opening slit 161 extending in an upper-to-lower direction. In the initial state of the catheter assembly 10D, the inner needle 12 is inserted into the slit 161. A proximal end portion of the body portion 162 is provided with an opening 163 configured to receive a portion of the catheter hub 149.

Moreover, the catheter operation member 150 is provided with a slit 165 configured to receive the catheter 16. The slit 165 is formed across the body portion 162 and the tab 164. The catheter operation member 150 configured as described above is disengageable from the catheter 16 and the catheter hub 149 after having moved out of the housing 152.

In the initial state of the catheter assembly 10D, the tab 164 is exposed at an upper distal end portion of the housing 152, and is positioned on the distal end side with respect to the wire operation member 154. A user can hook one's finger on the tab 164 exposed through the housing 152, thereby performing desired operation for the catheter hub 149.

The housing 152 is in a box shape. The housing 152 extends along a longitudinal direction of the inner needle 12 and the catheter 16, and is configured elongated as a whole. The housing 152 is connected to the inner needle 12 on the proximal end side thereof. In the initial state of the catheter assembly 10D, the housing 152 houses a large portion (other portions than a distal end portion) of the catheter 16, the entirety of the catheter hub 149, and a large portion (other portions than the distal end portion) of the catheter operation member 150 so that these portions can move in the longitudinal direction.

Specifically, the housing 152 has a lower wall 170, side walls 172, 173 extending upward from both of right and left sides of the lower wall 170, an upper wall 171 coupling portions of the right and left side walls 172, 173 on the proximal end side with respect to a distal end region (hereinafter referred to as "side wall distal end portions 174"), and a back wall 176 coupling the lower wall 170, the upper wall 171, and the right and left side walls 172, 173.

The right and left side wall distal end portions 174 have a height lower than that of the proximal-end-side portions. The support plate 178 extending in an axial direction is provided between the right and left side wall distal end portions 174. The wire operation member 154 is operably supported by the support plate 178, and a distal end portion of the wire operation member 154 is wound around a distal end portion 179 (a first support portion) of the support plate 178.

The height of an upper surface of the support plate 178 is slightly lower than the height of upper edges of the right and left side wall distal end portions 174. The support pin 180 (a second support portion) extending in a right-to-left direction is provided above the catheter 16 on the proximal end side with respect to the support plate 178 in the housing 152. A proximal end portion of the wire operation member 154 is wound around the support pin 180.

A needle holding portion 182 configured to hold the proximal end side of the inner needle 12 is provided at a position (in an illustrated example, a proximal-end-side position with respect to the center of the housing 152 in the longitudinal direction) between a distal end portion and a proximal end portion of the housing 152. The needle holding portion 182 protrudes upward from the lower wall 170 between the right and left side walls 172, 173. In the initial state of the catheter assembly 10D, a proximal end surface of the catheter operation member 150 contacts a distal end surface of the needle holding portion 182.

As described above, the housing 152 holds the inner needle 12 in the needle holding portion 182. Thus, when the housing 152 is moved in the proximal end direction with respect to the catheter 16, the inner needle 12 is also moved with respect to the catheter 16 in the proximal end direction in association with movement of the housing 152. That is, the housing 152 has a function as a needle hub fixed to a proximal end of the inner needle 12.

The wire operation member 154 is an operation unit configured to perform the operation of inserting the guide wire 22 into a patient's blood vessel through the connection member 156 before the operation of inserting the catheter 16 into the blood vessel.

The wire operation member 154 is disposed at the housing 152 with a portion of the wire operation member 154 being exposed through the housing 152 in at least the distal end region of the housing 152, and exhibits flexibility. Moreover, the portion of the wire operation member 154 exposed through the housing 152 is operable in the axial direction. The distal end portion of the wire operation member 154 is folded back into the housing 152 at the distal end portion thereof. The wire operation member 154 has a portion configured to move into the housing 152 from a position at which the wire operation member 154 is exposed through the housing 152 in association with operation of the wire operation member 154 in the distal end direction.

In the present embodiment, the wire operation member 154 is a flexible endless member wound around the distal end portion 179 of the support plate 178 and the support pin 180 provided at the housing 152, and is disposed above the catheter 16 and the inner needle 12 at initial positions. More specifically, the wire operation member 154 is in the form of a crawler 155 (an endless belt).

The wire operation member 154 is wound around the distal end portion 179 of the support plate 178 and the support pin 180. Thus, tension is provided to such a portion between the distal end portion 179 and the support pin 180, and the entirety of the wire operation member 154 extends in the axial direction. Of the wire operation member 154, a portion extending between an upper portion of the distal end portion 179 and an upper portion of the support pin 180 will be hereinafter referred to as an "upper belt portion 184," and a portion extending between a lower portion of the distal end portion 179 and a lower portion of the support pin 180 will be hereinafter referred to as a "lower belt portion 186."

The wire operation member 154 is slidable in the axial direction on the support plate 178. The user contacts the portion of the wire operation member 154 exposed through the housing 152 in the distal end region of the housing 152 so that the wire operation member 154 can be operated in the axial direction (a front-to-back direction). In this state, the wire operation member 154 receiving downward pressing force from a finger of the user is supported from below by the support plate 178, and therefore, does not sink downward.

The wire operation member 154 may be made of a resin material (various rubber materials, elastomer, etc.) exhibiting relatively-low rigidity (a small coefficient of elasticity), i.e., a soft resin material, so that the portions wound around the distal end portion 179 of the support plate 178 and the support pin 180 are easily deformable upon operation of the wire operation member 154 in the axial direction.

In the initial state of the catheter assembly 10D, small protrusions 188 functioning as anti-slip portions upon operation by finger contact are provided at intervals in the axial direction on an upper surface of the upper belt portion 184, and a tab 190 protruding upward beyond the small protrusions 188 is provided at the upper surface of the upper belt portion 184. Note that one or both of the small protrusions 188 and the tab 190 are not necessarily provided.

The connection member 156 is a member configured to move the guide wire 22 in association with operation of the wire operation member 154 in the axial direction, and is a member equivalent to the guide wire hub 24. In the present embodiment, the connection member 156 is disposed in the housing 152. A distal end portion of the connection member 156 is coupled with the upper belt portion 184 of the wire operation member 154, and a proximal end portion of the connection member 156 is fixed to a proximal end portion of the guide wire 22.

More specifically, the wire operation member 154 is provided with an upwardly-protruding protrusion 192 as a coupling portion for the connection member 156. The distal end portion of the connection member 156 is provided with an upwardly-recessed portion 194 as a coupling portion for the wire operation member 154. By engagement between the protrusion 192 and the recessed portion 194, the wire operation member 154 and the connection member 156 are coupled together. Note that coupling between the wire operation member 154 and the connection member 156 is not limited to the above-described configuration, and may be made by other fitting structures, bonding, welding, etc., for example.

In the present embodiment, it is configured such that the guide wire 22 moves in the same direction as the direction of user's operation of the wire operation member 154. That is, when the wire operation member 154 is operated in the distal end direction with the wire operation member 154 being pushed with the finger, the connection member 156 is driven in the distal end direction, and accordingly, the guide wire 22 moves forward with respect to the inner needle 12. Conversely, when the wire operation member 154 is operated in the proximal end direction with the wire operation member 154 being pushed with the finger, the connection member 156 is driven in the proximal end direction, and accordingly, the guide wire 22 retracts with respect to the inner needle 12.

Moreover, the wire operation member 154 has a protrusion 196 protruding from an outer surface of the belt portion. As illustrated in FIGS. 19 and 22A, in the initial state of the catheter assembly 10D, the protrusion 196 protrudes in the distal end direction from the distal end portion of the wire operation member 154, and engages with an engagement raised portion 198 provided at the tab 164 of the catheter operation member 150.

Figure 21:
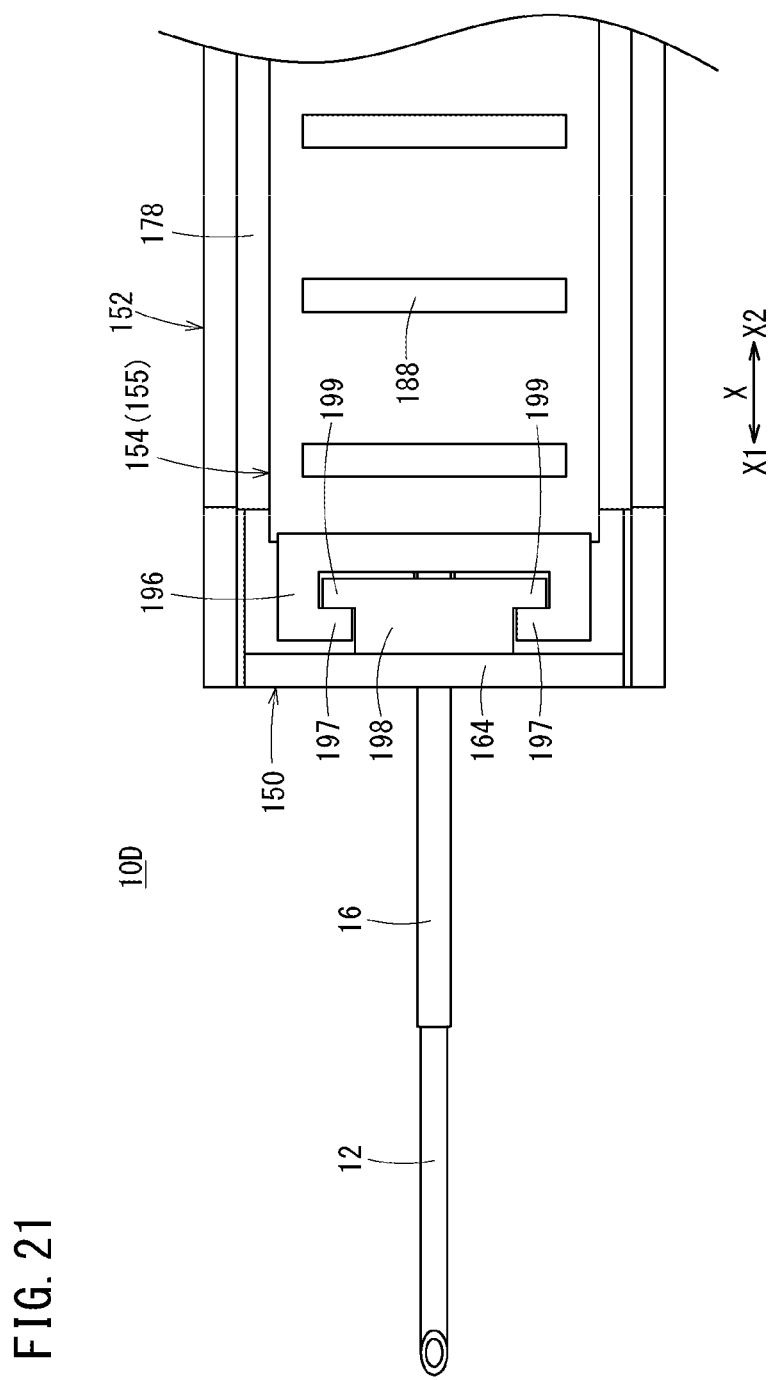
FIG. 21 is a plan view of a distal end side of the catheter assembly illustrated in FIG. 19.

Specifically, as illustrated in FIG. 21, the protrusion 196 has a pair of right and left inwardly-protruding first engagement claws 197, and the engagement raised portion 198 has right and left outwardly-protruding second engagement claws 199. The engagement raised portion 198 enters the protrusion 196, and the first engagement claws 197 engage respectively with the second engagement claws 199. Thus, in the initial state of the catheter assembly 10D, movement of the catheter operation member 150 with respect to the housing 152 in the distal end direction is inhibited.

In a state in which the guide wire 22 protrudes from a distal end of the inner needle 12 as illustrated in FIG. 22B (a state in which the connection member 156 is at a move-out position by operation of the wire operation member 154 in the distal end direction), the protrusion 196 protrudes toward the catheter operation member 150 (downward in the illustrated example) in the housing 152. At an initial position, the catheter operation member 150 does not contact the protrusion 196.

For properly transmitting axial drive force by operation of the wire operation member 154 to the guide wire 22, the connection member 156 is preferably made of a hard material. Such a hard material includes, for example, one or more materials selected from materials described as examples of a material forming the catheter hub 149 described above. The connection member 156 may be made of a metal material.

Next, features and advantageous effects of the catheter assembly 10D configured as described above will be described.

In the puncturing operation of puncturing a patient's skin with the catheter assembly 10D in the initial state illustrated in FIG. 22A, the user (a doctor, a nurse, etc.) grips the housing 152. Then, the skin is, toward the puncturing target blood vessel, punctured with a distal end portion (a distal end portion of the catheter 16 into which the inner needle 12 is inserted) of the catheter assembly 10D being pressed against a patient. In this manner, the skin is punctured with the distal end portions of the inner needle 12 and the catheter 16.

Next, in the state in which the skin is punctured with the distal end portions of the inner needle 12 and the catheter 16, the user holds the position of the housing 152 while operating, with the finger, the wire operation member 154 in the distal end direction. Specifically, the finger is pressed against the upper surface of the portion (in the present embodiment, a portion of the upper belt portion 184 close to the distal end) of the wire operation member 154 exposed through the housing 152, and then, the portion pressed by the finger is moved in the distal end direction.

In this state, the connection member 156 is pulled and driven in the distal end direction by operation of the wire operation member 154 as illustrated in FIG. 22B, and therefore, the guide wire 22 fixed to the connection member 156 is also moved in the distal end direction. Accordingly, a predetermined length of the guide wire 22 protrudes from the distal end of the inner needle 12. In association with movement of the guide wire 22 in the distal end direction and protrusion of the guide wire 22 from the distal end of the inner needle 12, the guide wire 22 is inserted into the blood vessel.

When the wire operation member 154 is operated in the distal end direction as described above, the position of the distal end portion of the wire operation member 154 does not change. That is, in association with operation of the wire operation member 154 in the distal end direction, the portion of the wire operation member 154 exposed through the housing 152 is folded back at the distal end portion 179 of the support plate 178, and moves into the housing 152. Thus, the position of the wire operation member 154 itself does not move with respect to the housing 152 in the distal end direction.

In association with operation of the wire operation member 154 in the distal end direction, the protrusion 196 provided at the wire operation member 154 moves from the distal end portion of the wire operation member 154 into the housing 152, and is brought into the state of protruding toward the catheter operation member 150.

A distal end portion of the guide wire 22 is inserted into a target position in the blood vessel. Subsequently, the user fixes, as illustrated in FIG. 23A, the position of the housing 152 while gripping the catheter operation member 150 to move the catheter member 158 (the catheter 16 and the catheter hub 149) forward. In this manner, the distal end of the catheter 16 is inserted into the target position in the blood vessel. Note that FIG. 23A illustrates the catheter member 158 in the middle of forward movement.

In this state, the catheter 16 moves forward in the blood vessel along an outer surface of the guide wire 22 inserted into the blood vessel in advance, i.e., moves forward following the guide wire 22. Note that when the catheter operation member 150 is moved forward, the body portion 162 is bent upward as illustrated in FIG. 23A, and therefore, the catheter 16 can be inserted into the blood vessel without difficulty.

In the middle of forward movement of the catheter operation member 150, the catheter operation member 150 (an inclined portion 162a of the body portion 162 in the present embodiment) comes into contact with the protrusion 196 provided at the wire operation member 154. Then, the catheter operation member 150 pushes and moves the protrusion 196 in the distal end direction in association with further movement of the catheter operation member 150 in the distal end direction, as illustrated in FIG. 23B.

In this state, the upper belt portion 184 of the wire operation member 154 moves in the direction opposite to the direction of movement of the protrusion 196, i.e., in the proximal end direction, and therefore, the guide wire 22 coupled with the upper belt portion 184 of the wire operation member 154 through the connection member 156 also moves in the proximal end direction. Accordingly, the guide wire 22 is pulled back, and a distal end of the guide wire 22 moves toward the proximal end side with respect to a distal end opening 30a of the inner needle 12. As described above, the wire operation member 154 forms a movement mechanism 92D configured to retract the connection member 156 (the guide wire hub) with respect to the housing 152 such that the distal end of the guide wire 22 is housed in the inner needle 12 in association with forward movement of the catheter hub 149 with respect to the housing 152.

Next, the user holds the positions of the catheter operation member 150 and the catheter member 158 while pulling the housing 152 in the proximal end direction. Accordingly, the catheter member 158 and the catheter operation member 150 are fully out of the housing 152, and the inner needle 12 fixed to the housing 152 is removed from the catheter 16. After the inner needle 12 has been removed from the catheter 16, the catheter operation member 150 may be detached from the catheter member 158. Note that after the inner needle 12 has been removed from the catheter 16, the catheter operation member 150 may remain attached to the catheter hub 149.

Next, a not-shown fluid transfusion tube connector is connected to the proximal end side of the catheter member 158 from which the inner needle 12 has been removed, and a transfusion material (a medical solution) is administered to the patient through a fluid transfusion tube.

As described above, according to the catheter assembly 10D of the present embodiment, when the catheter 16 moves with respect to the housing 152 in the distal end direction, the catheter operation member 150 pushes the protrusion 196 in the distal end direction, and accordingly, the wire operation member 154 is driven such that the distal end portion of the guide wire 22 moves with respect to the inner needle 12 toward the proximal end side of the distal end opening 30a of the inner needle 12. With this configuration, the distal end of the guide wire 22 is housed in the inner needle 12 in association with the operation of moving the catheter 16 with respect to the inner needle 12 in the distal end direction. This can inhibit spattering of blood adhering to the guide wire 22.

Moreover, in the case of the present embodiment, when the catheter 16 is moved with respect to the housing 152 in the distal end direction from the state in which the predetermined length of the distal end portion of the guide wire 22 protrudes from the distal end of the inner needle 12, pushing of the protrusion 196 begins after the catheter 16 has moved with respect to the guide wire 22 in the distal end direction by a predetermined distance. With this configuration, when the catheter 16 is inserted into the blood vessel, the guide wire 22 begins retracting after the catheter 16 has been inserted into the blood vessel along the outer surface of the guide wire 22. Thus, the guide wire 22 can be pulled back in association with the operation of moving out the catheter 16 without interference of a guide function of the guide wire 22.

Specifically in the case of the present embodiment, when the catheter 16 is moved with respect to the housing 152 in the distal end direction, the protrusion 196 is pushed in the distal end direction by the catheter operation member 150, and therefore, the mechanism configured to pull back the guide wire 22 in association with the operation of moving out the catheter 16 can be reliably built with a simple configuration.

In the case of the present embodiment, the distal end portion of the wire operation member 154 disposed in the distal end region of the housing 152 and exhibiting flexibility is folded back into the housing 152 at the distal end portion of the housing 152. Thus, even when the wire operation member 154 is operated in the distal end direction to move the guide wire 22 forward, the distal end position of the wire operation member 154 does not change. Thus, when operating the wire operation member 154, the user can grip the distal end region of the housing 152, and therefore, operability upon moving out of the guide wire 22 can be improved.

In the case of the present embodiment, the housing 152 has the first support portion (the distal end portion 179 of the support plate 178) provided at the distal end portion of the housing 152, and the second support portion (the support pin 180) provided on the proximal end side with respect to the first support portion. The wire operation member 154 is the endless member wound around the first support portion and the second support portion. With this configuration, when the wire operation member 154 formed of the endless member is operated in the distal end direction, the distal end portion of the wire operation member 154 is reliably folded back into the housing 152 by the first support portion of the housing 152, and therefore, the wire operation member 154 can be stably operated. Note that in the present embodiment, the configuration has been described, in which the wire operation member 154 is supported by two members of the support plate 178 and the support pin 180. However, the entire length of the support plate 178 may be extended, and the wire operation member 154 may be supported only by the support plate 178. In this case, the distal end portion of the support plate 178 functions as the first support portion, and a proximal end portion of the support plate 178 functions as the second support portion.

Moreover, the wire operation member 154 is formed of the endless member. Thus, the guide wire 22 can be pulled back in the proximal end direction by operation of the wire operation member 154 in the proximal end direction during or after moving out of the guide wire 22. In this case, operation of the wire operation member 154 in the proximal end direction is facilitated by operation performed with the finger contacting the tab 190.

Further, in the case of the present embodiment, even after the guide wire 22 has been pulled into the inner needle 12 in association with forward movement of the catheter member 158 (after activation of a guide wire pull-in mechanism), a state before activation of the guide wire pull-in mechanism can be brought. Specifically, the catheter operation member 150 or the catheter member 158 is retracted so that the state before forward movement of the guide wire 22 can be restored. Thus, the user can perform again the operation of inserting the guide wire 22 into the blood vessel and the operation of inserting the catheter member 158 into the blood vessel along the guide wire 22.

In addition, after the guide wire 22 has been pulled into the inner needle 12 in association with forward movement of the catheter member 158 (after activation of the guide wire pull-in mechanism), the wire operation member 154 is operated in the distal end direction so that the state before activation of the guide wire pull-in mechanism can be brought. Specifically, the wire operation member 154 is operated in the distal end direction with the finger contacting the tab 190. In this manner, the guide wire 22 protrudes from the distal end of the inner needle 12 again, and the protrusion 196 provided at the wire operation member 154 retracts the catheter operation member 150 and the catheter member 158. Thus, the user can perform again the operation of inserting the catheter member 158 into the blood vessel along the guide wire 22.

Further, the wire operation member 154 is in the form of the crawler 155. Thus, the wire operation member 154 configured such that the distal end position thereof does not change even upon operation in the distal end direction can be realized with a simple configuration. In addition, the user can contact the upper belt portion 184 of the crawler 155 exposed through the housing 152, thereby easily operating the crawler 155 in the axial direction. Consequently, operability of the wire operation member 154 is further improved.

In addition, in the case of the present embodiment, the connection member 156 moves the guide wire 22 in the same direction as the direction of user's operation of the wire operation member 154. With this configuration, the direction of operation of the wire operation member 154 and the direction of movement of the guide wire 22 are coincident with each other, and therefore, the guide wire 22 can be moved by intuitive operation. This leads to excellent operability.

Figure 24:
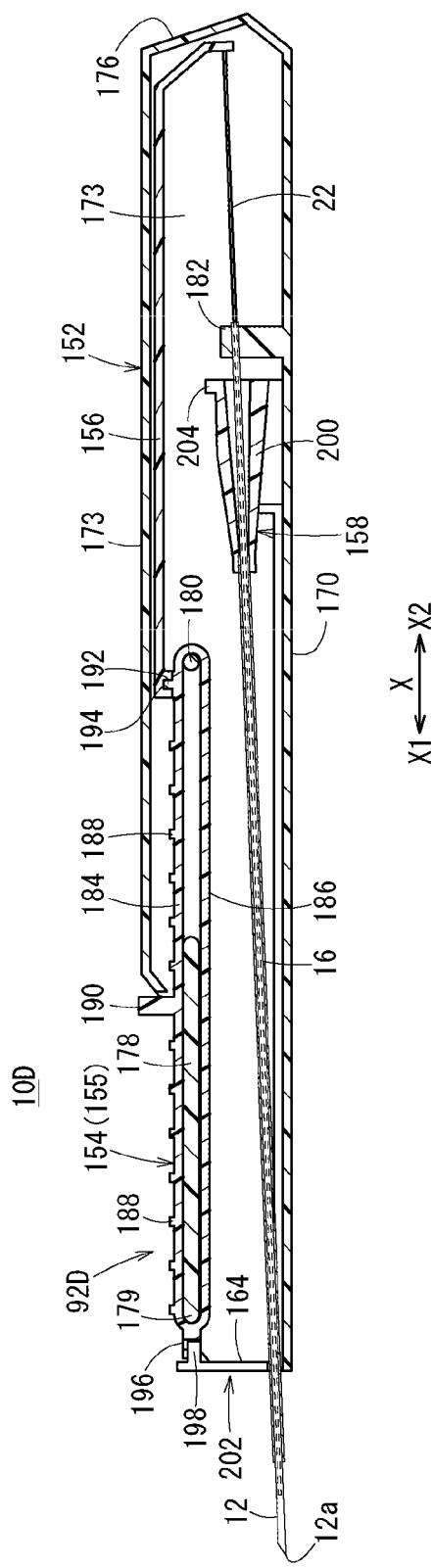
FIG. 24 is a sectional view of a catheter assembly of a variation of the fourth embodiment of the present invention.

In the catheter assembly 10D, a catheter hub 200 and a catheter operation member 202 illustrated in FIG. 24 may be employed instead of the catheter hub 149 and the catheter operation member 150 described above. An upper portion of the catheter hub 200 is provided with an upwardly-protruding raised portion 204.

In an illustrated example, the raised portion 204 protrudes upward from a proximal end portion of the catheter hub 200. The raised portion 204 may protrude upward from the distal-end-side position with respect to the proximal end portion of the catheter hub 200. The raised portion 204 does not contact the protrusion 196 with the catheter hub 200 being at an initial position. The proximal end portion of the catheter operation member 202 is rotatably and disengageably connected to the catheter hub 200.

In such use of the catheter assembly 10D including the catheter hub 200 provided with the raised portion 204, when the user operates the wire operation member 154 in the distal end direction such that the predetermined length of the distal end of the guide wire 22 protrudes from the distal end of the inner needle 12, the protrusion 196 provided at the wire operation member 154 moves into the housing 152 as in FIG. 22B. Next, the user moves the catheter hub 200 forward with respect to the housing 152 to insert the distal end of the catheter 16 to the target position in the blood vessel.

In this case, the raised portion 204 pushes the protrusion 196 in the distal end direction in the middle of forward movement of the catheter hub 200. Accordingly, the wire operation member 154 is driven such that the distal end portion of the guide wire 22 is moved with respect to the inner needle 12 toward the proximal end side of the distal end opening 30*a* of the inner needle 12. In association with the operation of moving the catheter 16 with respect to the inner needle 12 in the distal end direction as described above, the distal end of the guide wire 22 is housed in the inner needle 12. This can inhibit spattering of blood adhering to the guide wire 22.

Of the fourth embodiment, portions common to the third embodiment provide features and advantageous effects identical or similar to those of the third embodiment.

In the above-described first to fourth embodiments, the guide wire hub (the guide wire hub 24, the connection member 156) is fixed to the proximal end portion of the guide wire 22. However, in a variation, the guide wire hub is not necessarily fixed to the proximal end portion of the guide wire 22. In the case of this variation, the end portion of the guide wire 22 guided out of the proximal end side of the inner needle 12 is fixed to the needle hub (the housings 14, 152) or the inner needle 12, for example. Moreover, the guide wire hub is provided with a guide portion in the form of a curved hole configured such that the guide wire 22 extending from the needle hub in the proximal end direction is folded back toward the inner needle 12 and that the guide wire 22 is slidably guided and supported. The guide wire 22 is inserted into the guide portion. In this configuration, when the guide wire hub is moved forward with respect to the needle hub after the patient's skin has been punctured with the distal end portions of the inner needle 12 and the catheter 16, the guide wire 22 slides in the guide portion while being pushed in the distal end direction by the guide portion, and therefore, the guide wire 22 moves forward with respect to the inner needle 12. Accordingly, only the predetermined length of the guide wire 22 protrudes from the needle tip 12*a* of the inner needle 12. Moreover, when the catheter hub 18, 149, 200 is moved forward with respect to the needle hub to insert the catheter 16 to the target position in the blood vessel and the needle hub is retracted with respect to the catheter member 19, 158 in the proximal end direction to remove the inner needle 12 from the catheter 16, the guide wire 22 is pulled in the proximal end direction by the above-described guide portion of the guide wire hub, and accordingly, the guide wire 22 retracts with respect to the inner needle 12. In this manner, the distal end portion of the guide wire 22 is housed in the inner needle 12.

Certain embodiments of the present invention have been described above, but the present invention is not limited to the above-described embodiments. Needless to say, various modifications can be made without departing from the gist of the present invention.

What is claimed is:

1. A catheter assembly comprising:

a catheter;

a catheter hub fixed to a proximal end portion of the catheter;

a hollow inner needle having a needle tip and disengageably located in the catheter;

a needle hub fixed to a proximal end portion of the inner needle;

a guide wire slidably located in the inner needle, the guide wire being longer than the catheter and having a distal end that is protrudable from the needle tip;

a guide wire hub configured to support the guide wire and move the guide wire with respect to the inner needle in association with a movement of the guide wire hub; and a movement mechanism comprising:

a movable member configured to move forward with respect to the needle hub in association with a forward movement of the catheter hub with respect to the needle hub, and a gear mechanism configured to convert, through a gear wheel, with the forward movement of the movable member with respect to the needle hub into retraction movement of the guide wire hub with respect to the needle hub such that the distal end of the guide wire is housed in the inner needle in association with the forward movement of the catheter hub with respect to the needle hub.

2. The catheter assembly according to claim 1, wherein: the gear mechanism comprises:

a force transmitter configured to transmit force to the guide wire hub in association with a movement of the catheter hub, and the gear wheel configured to change a direction of the force of the force transmitter.

3. The catheter assembly according to claim 1, wherein: the gear mechanism comprises:

a first rack portion configured to move together with the guide wire hub, a second rack portion configured to move together with the movable member, and the gear wheel rotatably supported by the needle hub, and when the movable member moves forward with respect to the needle hub, force of forward movement of the second rack portion is transmitted to the first rack portion through the gear wheel, and accordingly, the first rack portion retracts.

4. The catheter assembly according to claim 3, wherein:

in a state in which the second rack portion is at an initial position with respect to the needle hub, the second rack portion does not engage with the gear wheel, and after the second rack portion has moved forward with respect to the needle hub by a predetermined distance, the second rack portion engages with the gear wheel.

5. The catheter assembly according to claim 1, wherein the movable member defines at least a portion of a protector, the protector is disengageably coupled with the catheter hub, the protector is movable relative to the needle hub in an axial direction, and the protector covers at least the needle tip of the inner needle in association with removal of the inner needle from the catheter.

6. The catheter assembly according to claim 1, wherein:

when the catheter is moved forward with respect to the inner needle with a predetermined length of a distal end portion of the guide wire protruding from the needle tip, the movement mechanism retracts the guide wire hub with respect to the needle hub after the catheter has moved forward with respect to the guide wire by a predetermined distance.

7. A method comprising:

providing a catheter assembly comprising:

a catheter;

a catheter hub fixed to a proximal end portion of the catheter;

a hollow inner needle having a needle tip and disengageably located in the catheter;

a needle hub fixed to a proximal end portion of the inner needle;

a guide wire slidably located in the inner needle, the guide wire being longer than the catheter and having a distal end that is protrudable from the needle tip;

a guide wire hub configured to support the guide wire and move the guide wire with respect to the inner needle in association with a movement of the guide wire hub;

a movement mechanism comprising:

a movable member configured to move forward with respect to the needle hub in association with a forward movement of the catheter hub with respect to the needle hub, and the gear mechanism configured to convert, through a gear, the forward movement of the movable member with respect to the needle hub into a retraction movement of the guide wire hub with respect to the needle hub such that the distal end of the guide wire is housed in the inner needle in association with the forward movement of the catheter hub with respect to the needle hub;

puncturing a blood vessel of a patient using the inner needle;

moving the guide wire from the inner needle into the blood vessel;

moving the catheter into the blood vessel along the guide wire;

removing the inner needle from the catheter; and moving the catheter hub forward with respect to the needle hub such that the movable member moves forward with respect to the needle hub, the gear mechanism converts the forward movement of the movable member with respect to the needle hub into the retraction movement of the guide wire hub with respect to the needle hub, and the distal end of the guide wire is housed in the inner needle.

* * * * *